US006878805B2

(12) United States Patent
Manoharan et al.

(10) Patent No.: US 6,878,805 B2
(45) Date of Patent: Apr. 12, 2005

(54) PEPTIDE-CONJUGATED OLIGOMERIC COMPOUNDS

(75) Inventors: Muthiah Manoharan, Carlsbad, CA (US); Martin A. Maier, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 10/222,595

(22) Filed: Aug. 16, 2002

(65) Prior Publication Data

US 2004/0034191 A1 Feb. 19, 2004

(51) Int. Cl.[7] .................. A61K 38/02; A61K 38/10; C07K 2/00; C07K 7/08

(52) U.S. Cl. ................ 530/327; 514/2; 514/8; 514/13; 514/14; 514/15; 514/16; 514/44; 530/322; 530/328; 530/345; 536/23.1

(58) Field of Search .............. 424/178.2, 179.1; 514/2, 13, 14, 15, 16, 44, 8; 530/326, 345, 322, 327, 328; 536/23.1

(56) References Cited

U.S. PATENT DOCUMENTS

| | | | |
|---|---|---|---|
| 4,587,044 A | 5/1986 | Miller et al. ............... 530/211 |
| 4,605,735 A | 8/1986 | Miyoshi et al. ............... 536/27 |
| 4,667,025 A | 5/1987 | Miyoshi et al. ............... 536/27 |
| 4,762,779 A | 8/1988 | Snitman ........................ 435/6 |
| 4,789,737 A | 12/1988 | Miyoshi et al. ............... 536/27 |
| 4,824,941 A | 4/1989 | Gordon et al. ............... 530/403 |
| 4,828,979 A | 5/1989 | Klevan et al. ................ 435/6 |
| 4,835,263 A | 5/1989 | Nguyen et al. ............... 536/27 |
| 4,876,335 A | 10/1989 | Yamane et al. ............... 536/27 |
| 4,904,582 A | 2/1990 | Tullis ........................... 435/6 |
| 4,948,882 A | 8/1990 | Ruth ........................... 536/27 |
| 4,958,013 A | 9/1990 | Letsinger ..................... 536/27 |
| 5,082,830 A | 1/1992 | Brakel et al. ................. 514/44 |
| 5,109,124 A | 4/1992 | Ramachandran et al. ..... 536/27 |
| 5,112,963 A | 5/1992 | Pieles et al. .................. 536/27 |
| 5,118,802 A | 6/1992 | Smith et al. .................. 536/27 |
| 5,138,045 A | 8/1992 | Cook et al. ................... 536/663 |
| 5,214,136 A | 5/1993 | Lin et al. ...................... 514/44 |
| 5,218,105 A | 6/1993 | Cook et al. ............... 536/25.31 |
| 5,245,022 A | 9/1993 | Weis et al. ................. 536/24.5 |
| 5,254,469 A | 10/1993 | Warren, III et al. ......... 435/188 |
| 5,258,506 A | 11/1993 | Urdea ........................ 536/23.1 |
| 5,262,536 A | 11/1993 | Hobbs, Jr. ................... 546/25 |
| 5,272,250 A | 12/1993 | Spielvogel et al. ......... 530/300 |
| 5,292,873 A | 3/1994 | Rokita et al. ............... 536/24.3 |
| 5,317,098 A | 5/1994 | Shizuya et al. ............. 536/23.1 |
| 5,371,241 A | 12/1994 | Brush et al. ................ 549/220 |
| 5,391,723 A | 2/1995 | Priest ........................ 536/23.1 |
| 5,414,077 A | 5/1995 | Lin et al. ................... 536/24.3 |
| 5,416,203 A | 5/1995 | Letsinger ................. 536/25.34 |
| 5,451,463 A | 9/1995 | Nelson et al. ............... 428/402 |
| 5,486,603 A | 1/1996 | Buhr ........................ 536/24.3 |
| 5,510,475 A | 4/1996 | Agrawal et al. ........... 536/24.3 |
| 5,512,439 A | 4/1996 | Hornes et al. ................. 435/6 |
| 5,512,667 A | 4/1996 | Reed et al. ............... 536/24.31 |
| 5,514,785 A | 5/1996 | Van Ness et al. .......... 536/22.1 |
| 5,525,465 A | 6/1996 | Haralambidis et al. ........ 435/6 |
| 5,541,313 A | 7/1996 | Ruth ......................... 536/24.3 |
| 5,545,730 A | 8/1996 | Urdea et al. .............. 536/28.51 |
| 5,552,538 A | 9/1996 | Urdea et al. ............... 536/24.3 |
| 5,565,552 A | 10/1996 | Magda et al. ................. 534/11 |
| 5,567,810 A | 10/1996 | Weis et al. ................. 536/25.3 |
| 5,574,142 A | 11/1996 | Meyer, Jr. et al. ......... 536/23.1 |
| 5,578,717 A | 11/1996 | Urdea et al. ............... 536/26.1 |
| 5,578,718 A | 11/1996 | Cook et al. ............... 536/27.21 |
| 5,580,731 A | 12/1996 | Chang et al. .................. 435/6 |
| 5,585,481 A | 12/1996 | Arnold, Jr. et al. ...... 536/25.33 |
| 5,587,371 A | 12/1996 | Sessler et al. ............. 514/185 |
| 5,591,584 A | 1/1997 | Chang et al. .................. 435/6 |
| 5,595,726 A | 1/1997 | Magda et al. ............... 424/9.61 |
| 5,597,696 A | 1/1997 | Linn et al. .................... 435/6 |
| 5,599,923 A | 2/1997 | Sessler et al. ............. 540/145 |
| 5,599,928 A | 2/1997 | Hemmi et al. ............. 540/474 |
| 5,608,046 A | 3/1997 | Cook et al. ................ 536/23.1 |
| 5,688,941 A | 11/1997 | Cook et al. ................ 536/25.3 |
| 6,379,884 B2 * | 4/2002 | Wada et al. .................. 435/4 |
| 6,559,279 B1 * | 5/2003 | Manoharan et al. ........ 530/322 |
| 2003/0003584 A1 * | 1/2003 | Adams ....................... 435/458 |
| 2003/0148928 A1 * | 8/2003 | Beigelman et al. ............ 514/7 |
| 2004/0006203 A1 * | 1/2004 | Maier et al. ................ 530/333 |

FOREIGN PATENT DOCUMENTS

| | | |
|---|---|---|
| JP | 11-290073 | 10/1999 |
| WO | WO 93/07883 | 4/1993 |
| WO | WO 00/72869 A1 * | 12/2000 |

OTHER PUBLICATIONS

Drin et al. Translocation of the pAntp Peptide. . . biochemistry. vol. 40, No. 6, pp. 1824–1834 (2001).*

Villa et al. Inhibition of telomerase activity by a cell–penetrating peptide nucleic acid . . . FEBS Letters. vol. 473, pp. 241–248 (2000).*

Copy of the PCT International Search Report dated Feb. 6, 2004 (PCT/US03/25567).

Auvray, P., et al., "PAAn–1b and PAAn–E: Two phosphorothioate antisense oligodeoxynucleotides inhibit human aromatase gene expression," *Biochem. Biophys. Res. Commun.*, 1998, 253, 1–9.

Bandyopadhyay, P., et al., "Nucleotide exchange in genomic DNA of rat hepatocytes using RNA/DNA oligonucleotides," *J. Biol. Chem.*, Apr. 9, 1999, 274(15), 10163–10172.

Crooke, S.T., et al., "Pharmacokinetic properties of several novel oligonucleotide analogs in mice," *J. Pharmacol. Exp. Ther.*, 1996, 277(2), 923–937.

(Continued)

*Primary Examiner*—Jeffrey Edwin Russel
(74) *Attorney, Agent, or Firm*—Woodcock Washburn LLP

(57) ABSTRACT

The present invention relates to novel amphipathic peptide-conjugated oligomeric compounds and to methods of making and using such compounds. The invention further relates to methods of enhancing the cellular uptake of oligomeric compounds comprising conjugating the compounds to amphipathic moieties such as amphipathic peptides.

38 Claims, 3 Drawing Sheets

OTHER PUBLICATIONS

Demeneix, B.A., et al., "Delivery of polynucleotides with polyamine lipids and polymers," *Nucleosides Nucleotides*, 1997, 16(7–9), 1121–1127.

Derossi, D., et al., "The third helix of the antennapedia homeodomain translocates through biological membranes," *The Journal of Biological Chemistry*, 1994, 269(14), 10444–10450.

Derossi, D., et al., "Cell internalization of the third helix of the antennapedia homeodomain is receptor–independent," *The Journal of Biological Chemistry*, 1996, 271(30), 18188–18193.

Dheur, S., et al., "Polyethylenimine but not cationic lipid improves antisense activity of 3'–capped phosphodiester oligonucleotides," *Antisense Nucleic Acid Drug Dev.*, 1999, 9, 515–525.

Dheur, S., et al., "Polyethyleneimine–mediated transfection to improve antisense activity of 3'–capped phosphodiester oligonucleotides," *Methods Enzymol.*, 1999, 313, 56–73.

Good, L., et al., "Bactericidal antisense effects of peptide–PNA conjugates," *Nature Biotechnology*, Apr. 2001, 19, 360–364.

Kabanov, A.V., "A new class of antivirals: antisense olgonucleotides combined with a hydrophobic substituent effectively inhibit influenza virus reproduction and synthesis of virus–specific proteins in MDCK cells," *FEBS Letts.*, 1990, 259, 327–330.

Kren, B.T., et al., Correction of the UDP–glucuronosyltransferase gene defect in the gunn rat model of crigler–najjar syndrome type 1 with a chimeric oligonucleotide, *Proc. Natl. Acad. Sci. U.S.A.*, Aug. 1999, 96, 10349–10354.

Letsinger, R. L. et al., "Cholesteryl–conjugated oligonucleotides: Synthesis, properties and activity as inhibitors of replication of human immunodeficiency virus in cell culture," *Proc. Natl. Acad. Sci.*, 1989, 86, 6553–6556.

Manoharan, M. et al., "Introduction of a Lipophilic Thioether Tether in the Minor Groove of Nucleic Acids for Antisense Applications," *Biorg. Med. Chem. Letts.*, 1993, 3(12), 2765–2770.

Manoharan M. et al., "Cholic Acid–Oligonucliotide Conjugates for Antisense Applications," *Bioorganic Med. Chem. Letts.*, 1994, 4, 1053–1060.

Manoharan, M. et al., "Chemical Modifications to Improve Uptake and Bioavailability of Antisense Oligonucleotides," *Annals NY Acad. Sciences*, 1992, 660, 306–309.

Manoharan, M. et al., "Lipidic Nucleic Acids." *Tetrahedron Letts.*, 1995, 36, 3651–3654.

Manoharan, M. et al., "Oligonucleotide Conjugates: Alteration of the Pharmacokinetic Properties of Antisense Agents," *Nucleosides and Nucleotides*, 1995, 14, 969–973.

Mishra, R. K. et al., "Improved leishmanicidal effect of phosphorotioate antisense oligonucleotides by LDL–medicated delivery," *Biochim. Et Biophysica*, 1995, 1264, 229–237.

Mitchell, D., et al., "Polyarginine enters cells more efficiently than other polycationic homopolymers," *J. Pepetides Res.*, 2000, 56, 318–325.

Oberhauser, B. et al., "Effective incorporation of 2'O–methyl–oligonucleotides into liposomes and enhanced cell association through modification with thiocholesterol," *Nucl. Acids Res.*, 1992, 20, 533–538.

Oehlke, J., et al., "Cellular uptake of an α–helical amphipathis model peptide with the potential to deliver polar compounds into the cell interior non–endocytically,," *J. Biochimica et Biophysica Acta*, 1998, 1414, 127–139.

Pillot, T., et al., "Fusogenic properties of the C–terminal domain of the alzheimer β–amyloid peptide," *J. Biol Chem.*, Nov. 15, 1996, 271(46), 28757–28765.

Pooga, M., et al., "Cellular translocation of proteins by transportan," *The FASEB J.*, 2001, Express Article 10.1096/fj.00–078fje, published online date Apr. 18, 2001, 13 pages.

Pooga, M., "Cell penetration by transportan," *The FASEB J.*, 1998, 12, 67–77.

Saison–Behmoaras, T. et al., "Short modified antisense oligonucleotides directed against Ha–ras point mutation induce selective cleavage of the mRNA and inhibit T24 cells proliferation." *EMBO J.*, 1991, 10, 1111–1118.

Schwarze, S., "In vivo protein transduction: delivery of a biologically active protein into the mouse," *Science*, 1999, 285, 1569–1572.

Schwarze, S., "Protein transduction: unrestricteddelivery into all cells?" *Trends in Cell Biology*, 2000, 10, 290–295.

Shea, R. G. et al., "Synthesis, hybridization properties and antiviral activity of lipid–oligodeoxynucletide conjugates," *Nucl. Acids Res.*, 1990, 18, 3777–3783.

Svinarchuk, F. P. et al., "Inhibition of HIV proliferation in MT–4 cells by antisense oligonucleotide conjugated to lipophilic groups," *Biochimie*, 193, 79, 49–54.

Tossi, A., "Amphipathic α–helical antimicrobial peptides," *Biopolymers(Peptide Science)*, 2000, 55, 4–30.

Vinogradov, S., et al., "Poly(ethylene glycol)–polyethyleneimine NanoGel™ particles: novel drug delivery systems for antisense oligonucleotides," *Colloids Surf. B*, 1999, 16, 291–304.

Vinogradov, S., et al., "Novel drug delivery systems: nanogel netwoks," *Polym. Prepr. (Am. Chem. Soc., Div. Polym. Chem.)*, 2000, 41(20, 1641–1642.

Vivest, E., "A truncated HIV–1 tat protein basic domain rapidly translocates through the plasma membrane and accumulates in the cell nucleus," *The Journal of Biological Chemistry*, 1997, 272(25), 16010–16017.

Wender, P., "The design, synthesis, and evaluation of molecules that enable or enhance cellular uptake: peptoid molecular transorters," *PNAS*, 2000, 97(24), 13003–13008.

\* cited by examiner

PEPTIDE-CONJUGATED OLIGOMERIC COMPOUNDS

FIELD OF THE INVENTION

The present invention is directed to peptide-conjugated oligomeric compounds and to methods of making and using such compounds.

BACKGROUND OF THE INVENTION

Nearly all disease states in multicellular organisms involve the action of proteins. Classic therapeutic approaches have focused on the interaction of proteins with other molecules in efforts to moderate the proteins disease-causing or disease-potentiating activities. In newer therapeutic approaches, modulation of the production of proteins has been sought. A general object of some current therapeutic approaches is to interfere with, or otherwise modulate, gene expression.

One method for inhibiting the expression of specific genes involves the use of oligonucleotides, particularly oligonucleotides that are complementary to a specific target messenger RNA (mRNA) sequence, known as antisense oligonucleotides. Several oligonucleotides are currently undergoing clinical trials for such use. Phosphorothioate antisense oligonucleotides are presently being used as antiviral agents in human clinical trials.

Oligonucleotides and their analogs can be designed to have particular properties. A number of chemical modifications have been introduced into oligomeric compounds to increase their usefulness as therapeutic agents. Such modifications include those designed to increase binding affinity to a target strand, to increase cell penetration, to stabilize against nucleases and other enzymes that degrade or interfere with the structure or activity of the oligonucleotide, to provide a mode of disruption (terminating event) once the oligonucleotide is bound to a target, and to improve the pharmacokinetic properties of the oligonucleotide. Despite such modifications, the cellular uptake of oligomeric compounds remains poor.

Oligonucleotides have been formulated with various with transfection agents, including anionic and cationic lipids and polyamines, in an attempt to improve their ability to permeate biological membranes. Dheur, S.; Saison-Behmoaras, T. E. *Methods Enzymol.* 2000, 313, 56–73; Vinogradov, S.; Batrakova, E.; Kabanov, A. V. *Polym. Prepr.* (Am. Chem. Soc., Div. Polym. Chem.) 2000, 41, 1641–1642; Vinogradov, S.; Batrakova, E.; Kabanov, A. *Colloids Surf., B* 1999, 16, 291–304; Bandyopadhyay, P.; Ma, X.; Linehan-Stieers, C.; Kren, B. T.; Steer, C. J. *J. Biol. Chem.* 1999, 274, 10163–10172; Auvray, P.; Sourdaine, P.; Seralini, G. E. *Biochem. Biophys. Res. Commun.* 1998, 253, 1–9; Demeneix, B. A.; Boussif, O.; Zanta, M. A.; Remy, J. S.; Behr, J. P. *Nucleosides Nucleotides* 1997, 16, 1121–1127. Of the transfection agents used, polyethylenimines (PEI) are generally the most efficient and least expensive delivery vehicles. Kren, B. T.; Parashar, B.; Bandyopadhyay, P.; Chowdhury, N. R.; Chowdhury, J. R.; Steer, C. J. *Proc. Natl. Acad. Sci. U. S. A.* 1999, 96, 10349–10354. It was observed, however, that, although complexes of excess PEI and oligonucleotide phosphorothioates were efficiently taken up by cells, the oligonucleotides failed to dissociate in the cytoplasm, resulting in no appreciable enhancement in the antisense activity of the oligonucleotides. Dheur, S.; Dias, N.; Van Aerschot, A.; Herdewijn, P.; Bettinger, T.; Remy, J.-S.; Helene, C.; Saison-Behmoaras, E. T. *Antisense Nucleic Acid Drug Dev.* 1999, 9, 515–525.

A need therefore exists in the art for the development of means to improve the cellular uptake and cellular distribution of oligomeric compounds.

SUMMARY OF THE INVENTION

In certain embodiments, the present invention relates to oligomeric compounds having at least one peptide covalently bound thereto, wherein said peptide comprises from about 8 to about 20 amino acids and is capable of forming an α-helical structure having at least one hydrophobic face and at least one hydrophilic face. In certain preferred embodiments, the present invention relates to oligomeric compounds having formula I:

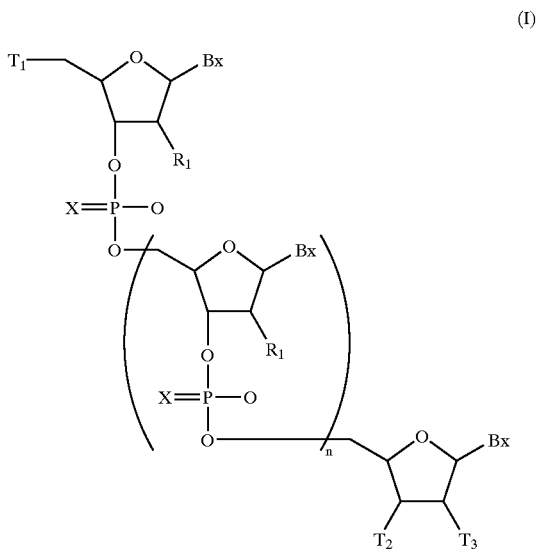

wherein:
one of $T_1$, $T_2$, and $T_3$ is L—$R_2$;
another of $T_1$, $T_2$, and $T_3$ is hydrogen, hydroxyl or a protected hydroxyl;
the remaining of $T_1$, $T_2$, and $T_3$ is hydrogen, L—$R_2$ or an optionally protected sugar substituent group;
  each L is a linking moiety;
  each $R_2$ is said amphipathic peptide;
  each Bx is an optionally protected heterocyclic base moiety;
  each $R_1$ is, independently, hydrogen or an optionally protected sugar substituent group;
  each X is, independently, S or O; and
  n is from 2 to about 50.

In certain other preferred embodiments, the present invention relates to oligomeric compounds having formula IV:

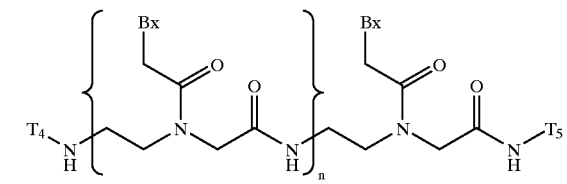

wherein:
each $T_4$ and $T_5$ is, independently, —L—$R_2$, hydrogen, an amino protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl, provided that at least one of $T_4$ and $T_5$ is —L—$R_2$;

each Bx is an optionally protected heterocyclic base moiety;

n is from 2 to about 50;

L is a linking moiety; and $R_2$ is said amphipathic peptide.

In other embodiments, the invention relates to oligomeric compounds having at least one peptide covalently bound thereto, wherein said peptide comprises from about 8 to about 20 amino acids and is capable of forming an α-helical structure having at least one hydrophobic face and at least one hydrophilic face, and the oligomeric compounds further comprise at least one targeting moiety covalently attached thereto.

DETAILED DESCRIPTION OF THE PREFERRED EMBODIMENTS

Figure 1:
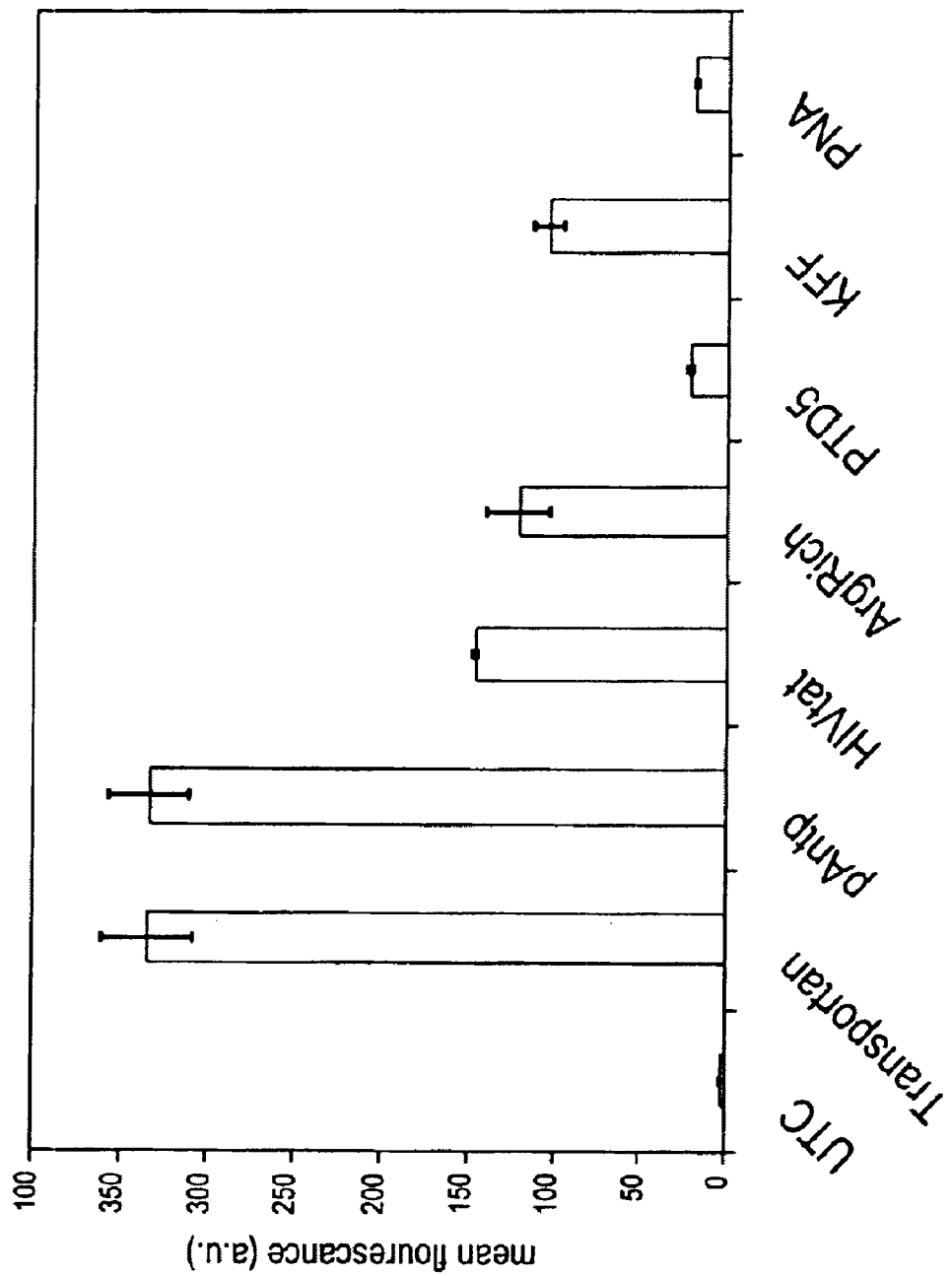
FIG. 1 shows the mean fluorescence of cells incubated with known cellular permeation peptides.

In the context of this invention, the term "oligomeric compound" refers to a polymeric structure capable of hybridizing a region of a nucleic acid molecule. This term includes oligonucleotides, oligonucleosides, oligonucleotide analogs, modified oligonucleotides and oligonucleotide mimetics. Oligomeric compounds can be prepared to be linear or circular and may include branching. They can be prepared single stranded or double stranded and may include overhangs. In general an oligomeric compound comprises a backbone of linked momeric subunits where each linked momeric subunit is directly or indirectly attached to a heterocyclic base moiety. The linkages joining the monomeric subunits, the monomeric subunits and the heterocyclic base moieties can be variable in structure giving rise to a plurality of motifs for the resulting oligomeric compounds including hemimers, gapmers and chimeras.

Oligomeric compounds according to the present invention preferably comprise from about 5 to about 50 monomer subunits and, hence, about 5 to about 50 nucleosidic bases. It is more preferred that such compounds comprise from about 8 to about 30 monomer subunits, with 15 to 25 monomer subunits being particularly preferred. In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The terms "oligonucleotide analog" and "modified oligonucleotide" refers to oligonucleotides that have one or more non-naturally occurring portions which function in a similar manner to oligonucleotides. Such modified or substituted oligonucleotides are often preferred over native forms because of desirable properties such as, for example, enhanced cellular uptake, enhanced affinity for nucleic acid target and increased stability in the presence of nucleases.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure. However, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

In the context of this invention, the term "oligonucleoside" refers to nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to, siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts.

Representative United States patents that teach the preparation of the above-noted oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

The present invention provides oligomeric compounds comprising a plurality of linked nucleosides wherein the preferred internucleoside linkage is a 3',5'-linkage. Alternatively, 2',5'-linkages can be used (as described in U.S. application Ser. No. 09/115,043, filed Jul. 14, 1998, now abandoned). A 2',5'-linkage is one that covalently connects the 2-position of the sugar portion of one nucleotide subunit with the 5'-position of the sugar portion of an adjacent nucleotide subunit.

The internucleotide linkage found in native nucleic acids is a phosphodiester linkage. This linkage has not been the linkage of choice for synthetic oligonucleotides that are for the most part targeted to a portion of a nucleic acid such as mRNA because of stability problems e.g. degradation by nucleases. Preferred internucleotide linkages and internucleoside linkages as is the case for non phosphate ester type linkages include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleoside linkages is a 3' to 3',5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above-noted phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In more preferred embodiments of the invention, oligomeric compounds have one or more phosphorothioate and/or heteroatom internucleoside linkages, in particular —CH$_2$—NH—O—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— [wherein the native phosphodiester internucleotide linkage is represented as —O—P(=O)(OH)—O—CH$_2$—]. The MMI type internucleoside linkages are disclosed in the above referenced U.S. Pat. No. 5,489,677. Preferred amide internucleoside linkages are disclosed in the above referenced U.S. Pat. No. 5,602,240.

Specific examples of preferred oligomeric compounds useful in this invention include those having modified backbones or non-naturally occurring internucleoside linkages. As defined in this specification, modified backbones include those having a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative Phosphorus-containing Linkages phosphorodithioate (—O—P(S)(S)—O—);
phosphorothioate (—O—P(S)(O)—O—);
phosphoramidate (—O—P(O)(NJ$_2$)—O—);
phosphonate (—O—P(J)(O)—O—);
phosphotriesters (—O—P(O J)(O)—O—);
phophosphoramidate (—O—P(O)(NJ)—S—);
thionoalkylphosphonate (—O—P(S)(J)—O—);
thionoalkylphosphotriester (—O—P(O)(OJ)—S—);
phosphoramidate (—N(J)—P(O)(O)—O—);
boranophosphate (—R$^5$—P(O)(O)—J—);

where J denotes a substituent group which is commonly hydrogen or an alkyl group or a more complicated group that varies from one type of linkage to another.

Representative United States patents that teach the preparation of the above-noted phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Representative Non-phosphorus-containing Linkages thiodiester (—O—C(O)—S—);
thionocarbamate (—O—C(O)(NJ)—S—);
siloxane (—O—Si(J)$_2$—O—);
carbamate (—O—C(O)—NH— and —NH—C(O)—O—)
sulfamate (—O—S(O)(O)—N— and —N—S(O)(O)—N—;
morpholino sulfamide (—O—S(O)(N(morpholino)-);
sulfonamide (—O—SO$_2$—NH—);
sulfide (—CH$_2$—S—CH$_2$—);
sulfonate (—O—SO$_2$—CH$_2$—);
N,N'-dimethylhydrazine (—CH$_2$—N(CH$_3$)—N(CH$_3$)—);
thioformacetal (—S—CH$_2$—O—);
formacetal (—O—CH$_2$—O—);
thioketal (—S—C(J)$_2$—O—); and
ketal (—O—C(J)$_2$—O—);
amine (—NH—CH$_2$—CH$_2$—);
hydroxylamine (—CH$_2$—N(J)—O—);

hydroxylimine (—CH=N—O—); and hydrazinyl (—CH$_2$—N(H)—N(H)—).

where J denotes a substituent group which is commonly hydrogen or an alkyl group or a more complicated group that varies from one type of linkage to another.

Representative United States patents that teach the preparation of the above-noted oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Particularly preferred are oligonucleotides with phosphorothioate backbones and oligonucleosides with heteroatom backbones, and in particular —CH$_2$—NH—O—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— [wherein the native phosphodiester backbone is represented as —O—P—O—CH$_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

In the context of this invention, the term "oligonucleotide mimetic" refers to an oligonucleotide wherein the backbone of the nucleotide units has been replaced with groups of somewhat equivalent function. Although the term is intended to include oligomeric compounds wherein only the furanose ring or both the furanose ring and the internucleotide linkage are replaced with novel groups, replacement of only the furanose ring is also referred to in the art as being a sugar surrogate. Oligonucleotide mimetics can be further modified to incorporate one or more modified heterocyclic base moieties to enhance properties such as hybridization.

One oligonucleotide mimetic that has been reported to have excellent hybridization properties, is peptide nucleic acids (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497–1500.

PNA has been modified to incorporate numerous modifications since the basic PNA structure was first prepared. The basic structure is shown below:

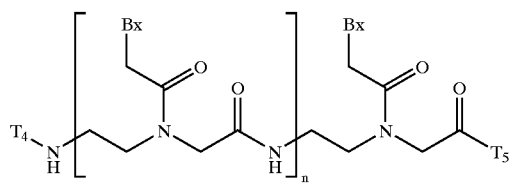

wherein

Bx is a heterocyclic base moiety;

T$_4$ is hydrogen, an amino protecting group, —C(O)R$_5$, substituted or unsubstituted C$_1$–C$_{10}$ alkyl, substituted or unsubstituted C$_2$–C$_{10}$ alkenyl, substituted or unsubstituted C$_2$–C$_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;

T$_5$ is —OH, —N(Z$_1$)Z$_2$, R$_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;

Z$_1$ is hydrogen, C$_1$–C$_6$ alkyl, or an amino protecting group;

Z$_2$ is hydrogen, C$_1$–C$_6$ alkyl, an amino protecting group, —C(=O)—(CH$_2$)$_n$—J—Z$_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

Z$_3$ is hydrogen, an amino protecting group, —C$_1$–C$_6$ alkyl, —C(=O)—CH$_3$, benzyl, benzoyl, or —(CH$_2$)$_n$—N(H)Z$_1$;

each J is O, S or NH;

R$_5$ is a carbonyl protecting group; and n is from 2 to about 50.

Peptide nucleic acids (PNAs) are prepared in accordance with any of the various procedures referred to in Peptide Nucleic Acids (PNA): Synthesis, Properties and Potential Applications, Bioorganic & Medicinal Chemistry, 1996, 4, 5–23. They may also be prepared in accordance with U.S. Pat. Nos. 5,539,082, 5,700,922, and 5,719,262, herein incorporated by reference.

PNA binds both DNA and RNA to form PNA/DNA or PNA/RNA duplexes. The resulting PNA/DNA or PNA/RNA duplexes are bound with greater affinity than corresponding DNA/DNA or DNA/RNA duplexes as determined by Tm's. This high thermal stability might be attributed to the lack of charge repulsion due to the neutral backbone in PNA. The neutral backbone of the PNA also results in the Tm's of PNA/DNA(RNA) duplex being practically independent of the salt concentration. Thus the PNA/DNA duplex interaction offers a further advantage over DNA/DNA duplex interactions which are highly dependent on ionic strength. Homopyrimidine PNAs have been shown to bind complementary DNA or RNA forming (PNA)2/DNA(RNA) triplexes of high thermal stability (see, e.g., Egholm, et al., Science, 1991, 254, 1497; Egholm, et al., J. Am. Chem. Soc., 1992, 114, 1895; Egholm, et al., J. Am. Chem. Soc., 1992, 114, 9677).

The binding of a PNA strand to a DNA or RNA strand can occur in one of two orientations. The orientation is said to be anti-parallel when the DNA or RNA strand in a 5' to 3' orientation binds to the complementary PNA strand such that the carboxyl end of the PNA is directed towards the 5' end of the DNA or RNA and amino end of the PNA is directed towards the 3' end of the DNA or RNA. In the parallel orientation the carboxyl end and amino end of the PNA are just the reverse with respect to the 5'-3' direction of the DNA or RNA.

PNAs bind to both single stranded DNA and double stranded DNA. As noted above, in binding to double stranded DNA it has been observed that two strands of PNA can bind to the DNA. While PNA/DNA duplexes are stable in the antiparallel configuration, it was previously believed that the parallel orientation is preferred for $(PNA)_2$/DNA triplexes.

The binding of two single stranded pyrimidine PNAs to a double stranded DNA has been shown to take place via strand displacement, rather than conventional triple helix formation as observed with triplexing oligonucleotides. When PNAs strand invade double stranded DNA, one strand of the DNA is displaced and forms a loop on the side of the $PNA_2$/DNA complex area. The other strand of the DNA is locked up in the $(PNA)_2$/DNA triplex structure. The loop area (alternately referenced as a D loop) being single stranded, is susceptible to cleavage by enzymes that can cleave single stranded DNA.

A further advantage of PNA compared to oligonucleotides is that their polyamide backbone (having appropriate nucleobases or other side chain groups attached thereto) is not recognized by either nucleases or proteases and are not cleaved. As a result PNAs are resistant to degradation by enzymes unlike DNA and peptides.

Because of their properties, PNA are known to be useful in a number of different areas. Since PNAs having stronger binding and greater specificity than oligonucleotides, they are used as probes in cloning, blotting procedures, and in applications such as fluorescence in situ hybridization (FISH). Homopyrimidine PNAs are used for strand displacement in homopurine targets. The restriction sites that overlap with or are adjacent to the D-loop will not be cleaved by restriction enzymes. Also, the local triplex inhibits gene transcription. Thus in binding of PNAs to specific restriction sites within a DNA fragment, cleavage at those sites can be inhibited. Advantage can be taken of this in cloning and subcloning procedures. Labeled PNAs are also used to directly map DNA molecules. In effecting this, PNA molecules having a fluorescent label are hybridized to complementary sequences in duplex DNA using strand invasion.

In accordance with this invention, it has been found that the most stable triplexes that are formed between two single stranded PNAs or a bis PNA and a DNA or RNA target strand are triplexes wherein the Watson/Crick base pairing strand is in an anti-parallel orientation relative to the target strand and the Hoogsteen base pairing strand is in a parallel orientation relative to the target strand. As so orientated to the target strand, the two PNA strands are therefore antiparallel to each other.

Bis PNAs have shown improved binding affinity, thermal stability, and specificity over single stranded PNAs. Using dsDNA as a target it has been shown that the preferred orientation is with the first PNA strand of the bis PNA parallel to the target, i.e. the target DNA strand of the duplex is referenced in a 5' to 3' direction and the first PNA is complementary in an N to C direction, and the second PNA strand of the bis PNA is antiparallel to the target, i.e. it is complementary to the DNA strand (again referenced in a 5' to 3' direction) in a C to N direction. Thus the linking segment connects the PNA strands in opposite orientation to each other, i.e. from a common reference point, one strand is lined up in a N to C direction and the other is lined up in a C to N direction.

Although we do not wish to be bound by theory, it is believed that the antiparallel strand of the bis PNA binds the DNA target thereby displacing the other DNA strand via strand invasion. This binding is of a Watson/Crick nature. The second PNA strand of the bis PNA, the parallel strand, now binds the DNA using Hoogsteen type hydrogen bonding. It has been shown using the component single stranded PNAs and comparing them separately and as a mixture to the bis PNA that the bis PNA has a faster on rate e.g. it binds faster to the target. This faster on rate is attributed to the enforced close proximity of the second strand in the bis PNA.

We have also studied the effect of pH on the Tm of bis PNA bound to dsDNA as compared to the same bis PNA with the cytosines replaced with pseudo isocytosines. It has been observed in previous studies that there is a pronounced dependence on pH for binding of PNA to dsDNA. The decrease in Tm with higher pH shows that Hoogsteen binding in a $(PNA)_2$/DNA complex is pH dependent. Normal Hoogsteen binding requires that the cytosines be protonated. This makes the Hoogsteen strand binding pH dependent. We have found that replacement of one or more of the cytosine nucleobases in a Hoogsteen strand with pseudo isocytosine and other like nucleobases removes this dependence. To demonstrate this effect, in two bis PNAs of the invention, one was synthesized such that the cytosines nucleobases in the parallel strand were replaced with pseudo isocytosines and the other was synthesized such that the cytosines in the antiparallel strand were replaced with pseudo isocytosines. The bis PNA with the pseudo isocytosines in the parallel strand showed almost no dependence on pH indicating that the parallel strand is involved with Hoogsteen binding.

The replacement of cytosine by pseudo isocytosine or other like C-pyrimidine nucleobases is effected in a straight forward manner as per certain of the examples set forth below. This is in direct contrast with replacement of cytosine with pseudo isocytosine or other C-pyrimidines in nucleosides. In nucleosides, an anomeric specific carbon-carbon bond must be formed in synthesizing the C-nucleoside. Since there are no anomeric (sugar) carbon atoms in peptide nucleic acids, such constraints need not be considered.

The triple helix principle is used in the art for sequence-specific recognition of dsDNA. Triple helix formation utilizes recognition of homopurine-homopyrimidine sequences. A strand displacement complex with triple helix formation is superior to simple triple helix recognition in that strand displacement complexes are very stable at physiological conditions, that is, neutral pH, ambient (20–40 □C.) temperature and medium (100–150 mM) ionic strength.

Sequence-specific recognition of ssDNA by base complementary hybridization can likewise be exploited to target specific genes and viruses. In this case, the target sequence is contained in the mRNA such that binding of the drug to the target hinders the action of ribosomes and, consequently, translation of the mRNA into protein. The bis PNAs of the invention are superior to prior reagents in that they have significantly higher affinity for complementary ssDNA. Also, they can be synthesized such that they possess no charge and are water soluble, which should facilitate cellular uptake, and they contain amides of non-biological amino acids, which should make them biostable and resistant to enzymatic degradation by, for example, proteases.

Modification of the PNA backbone is also contemplated by the present invention. In one embodiment the methylene group of the glycyl portion of the aminoethyl glycyl backbone is substituted with a functional group. The resulting PNA oligomer has the formula:

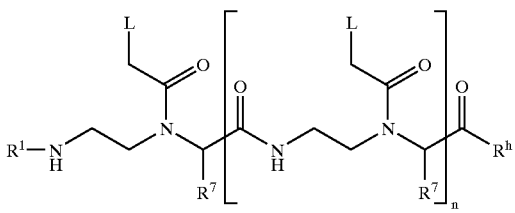

wherein:
each L is, independently, a heterocyclic base moiety;
each $R^7$ is, independently, hydrogen or $C_1$–$C_8$ alkylamine;
$R^h$ is OH, $NH_2$ a protected amino group or $NHLysNH_2$;
$R^i$ is H, or an amino protecting group such as $COCH_3$ or t-butoxycarbonyl; and
n is an integer from 1 to about 50.

The preparation of this group of PNA oligomers is described in U.S. Pat. No. 5,719,262, issued Feb. 17, 1998, hereby incorporated by reference in its entirety.

Further PNA backbone substitutions at the glycinyl methylene group are disclosed in U.S. Pat. No. 6,107,470, issued Aug. 22, 2000, hereby incorporated by reference in its entirety.

Further modification of the backbone including various combinations of substitution at the glycinyl methylene, varying the chain length of the aminoethyl group and or the glycinyl group, and the tethering group are amenable to the present invention. Included in this group of PNA oligomers are those having the formula:

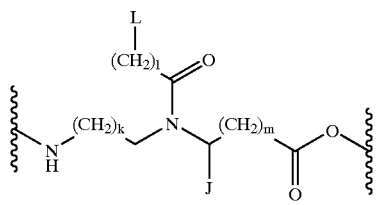

wherein each J is, independently, hydrogen or a side chain of a naturally occurring alpha amino acid;
k, m and l are each, independently, 0 or an interger from 1 to about 5; and
L is a heterocyclic base moiety.

The preparation of PNA compounds having these modifications are disclosed in U.S. Pat. No. 5,641,625, issued Jun. 24, 1997, hereby incorporated by reference in its entirety.

Further backbone modifications and substitutions are disclosed in U.S. Pat. No. 5,773,571, issued Jun. 30, 1998, hereby incorporated by reference in its entirety.

The preparation of PNA monomers and oligomers having a cyclic structure incorporated into the backbone wherein the cyclic structure could give chirality to two of the carbon atoms of the backbone is disclosed in U.S. Pat. Nos. 5,977,296, issued Nov. 2, 1999, and U.S. Pat. No. 6,201,103, issued Mar. 13, 2001, hereby incorporated by reference in their entirety.

PNA has been used for many therapeutic and genetic applications, including monitoring telomere length, screening for genetic mutations, affinity capture of nucleic acids, and antisense-mediated target reduction. Such applications are described in Corey, D. R. (1997) in Trends Biotechnol. pp 224–229; Lansdorp, P. M., Verwoerd, N. P., van de Rijke, F. M., Dragowska, V., Little, M.-T., Dirks, R. W., Raap, A. K., and Tanke, H. J. (1996) Hum. Mol. Genet. 5, 685–691; Orum, H., Nielsen, P. E., Egholm, M., Berg, R. H., Buchardt, O., and Stanley, C. (1993) Nucleic Acids Research 21, 5332–6; Carlsson, C., Jonsson, M., Norden, B., Dulay, M. T., Zare, R. N., Noolandi, J., Nielsen, P. E., Tsui, L.-C., and Zielenski, J. (1996) in Nature (London) pp 207; Bukanov, N. O., Demidov, V. V., Nielsen, P. E., and Frank-Kamenetskii, M. D. (1998) Proceedings of the National Academy of Sciences of the United States of America 95, 5516–20; and Norton, J. C., Piatyszek, M. A., Wright, W. E., Shay, J. W., and Corey, D. R. (1996) Nat. Biotechnol. 14, 615–19.

Besides binding target mRNA with high affinity, PNAs are highly resistant to nuclease and protease degradation, and display mismatch sequence discrimination, thus making them interesting third generation antisense molecules with potential therapeutic application. Such properties are described in Norton, J. C., Piatyszek, M. A., Wright, W. E., Shay, J. W., and Corey, D. R. (1996) Nat. Biotechnol. 14, 615–19; and Egholm, M., Buchardt, O., Christensen, L., Behrens, C., Freier, S. M., Driver, D. A., Berg, R. H., Kim, S. K., Norden, B., and Nielsen, P. E. (1993) Nature (London) 365, 566–8.

PNA oligomers have demonstrated in vitro transcriptional and translational block of many genes, as described in Mologni, L., Nielsen, P. E., and Gambacorti-Passerini, C. (1999) Biochem. Biophys. Res. Commun. 264, 537–543. Furthermore, PNA oligomers have been shown to induce triplex mediated mutagenesis of a chromosomal gene in mouse cells, as described in Faruoi, A. F., Egholm, M., and Glazer, P. M. (1998) Proc. Natl. Acad. Sci. U. S. A. 95, 1398–1403.

Another class of oligonucleotide mimetics that has been studied is based on linked morpholino units (morpholino nucleic acid) having heterocyclic bases attached to the morpholino ring. A number of linking groups have been reported that link the morpholino monomeric units in a morpholino nucleic acid. A preferred class of linking groups have been selected to give a non-ionic oligomeric compound. The non-ionic morpholino-based oligomeric compounds are less likely to have undesired interactions with cellular proteinsMorpholino-based oligomeric compounds are non-ionic mimics of oligonucleotides which are less likely to form undesired interactions with cellular proteins (Dwaine A. Braasch and David R. Corey, Biochemistry, 2002, 41 (14), 4503–4510). Morpholino-based oligomeric compounds are disclosed in U.S. Pat. No. 5,034,506, issued Jul. 23, 1991. The morpholino class of oligomeric compounds have been prepared having a variety of different linking groups joining the monomeric subunits.

Morpholino nucleic acids have been prepared having a variety of different linking groups ($L_2$) joining the monomeric subunits. The basic formula is shown below:

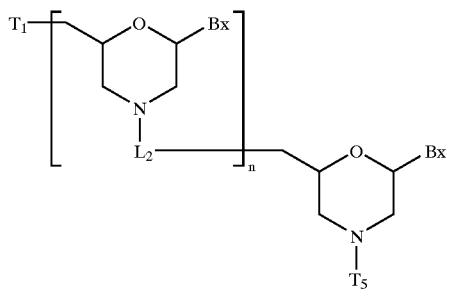

wherein
$T_1$ is hydroxyl or a protected hydroxyl;
$T_5$ is hydrogen or a phosphate or phosphate derivative;

$L_2$ is a linking group; and n is from 2 to about 50.

A further class of oligonucleotide mimetics is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.*, 2000, 122, 8595–8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. Coli* RNase resulting in cleavage of the target RNA strand.

The general formula of CeNA is shown below:

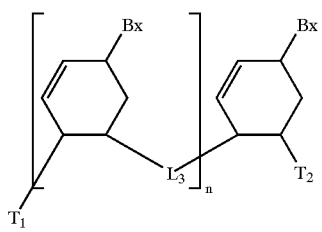

wherein each Bx is a heterocyclic base moiety;

$T_1$ is hydroxyl or a protected hydroxyl; and $T_2$ is hydroxyl or a protected hydroxyl.

Another class of oligonucleotide mimetics (anhydrohexitol nucleic acid) can be prepared from one or more anhydrohexitol nucleosides (see, Wouters and Herdewijn, *Bioorg. Med. Chem. Lett.*, 1999, 9, 1563–1566) and would have the general formula:

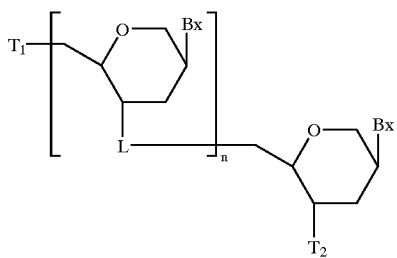

A further preferred modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage is preferably a methelyne (—CH2—)n group bridging the 2' oxygen atom and the 4' carbon atom wherein n is 1 or 2 (Singh et al., Chem. Commun., 1998, 4, 455–456). LNA and LNA analogs display very high duplex thermal stabilities with complementary DNA and RNA (Tm=+3 to +10 C.), stability towards 3'-exonucleolytic degradation and good solubility properties. The basic structure of LNA showing the bicyclic ring system is shown below:

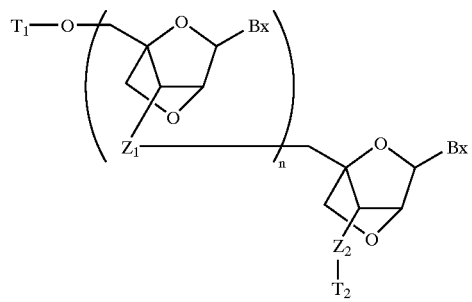

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44–53). These conformations are associated with improved stacking of the nucleobases (Wengel et al., Nucleosides Nucleotides, 1999, 18, 1365–1370).

LNA has been shown to form exceedingly stable LNA:LNA duplexes (Koshkin et al., J. Am. Chem. Soc., 1998, 120, 13252–13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-modified oligonucleotides, as well as the LNAs, are useful in a wide range of diagnostic and therapeutic applications. Among these are antisense applications, PCR applications, strand-displacement oligomers, substrates for nucleic acid polymerases and generally as nucleotide based drugs.

Potent and nontoxic antisense oligonucleotides containing LNAs have been described (Wahlestedt et al., Proc. Natl. Acad. Sci. U. S. A., 2000, 97, 5633–5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished.

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607–3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219–2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035–10039). In addition, 2'-Amino- and 2'-methylamino-LNA's have been prepared and the thermal stability of their duplexes with complementary RNA and DNA strands has been previously reported.

Further oligonucleotide mimetics have been prepared to include bicyclic and tricyclic nucleoside analogs having the formulas (amidite monomers shown):

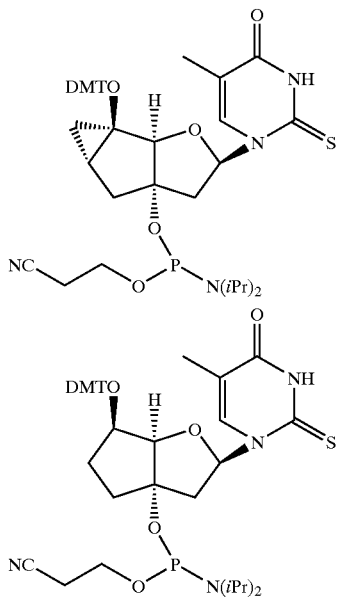

(see Steffens et al., Helv. Chim. Acta, 1997, 80, 2426–2439; Steffens et al., J. Am. Chem. Soc., 1999, 121, 3249–3255; and Renneberg et al., J. Am. Chem. Soc., 2002, 124, 5993–6002). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetics is referred to as phosphonomonoester nucleic acids incorporate a phosphorus group in a backbone the backbone. This class of oligonucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below.

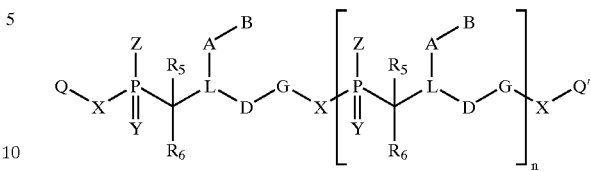

Another oligonucleotide mimetic has been reported wherein the furanosyl ring has been replaced by a cyclobutyl moiety.

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858–859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289–302, Crooke, S. T. and Lebleu, B., ed., CRC Press, 1993. Certain of these nucleobases are particularly useful for increasing the binding affinity of the oligomeric compounds of the invention. These include, 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., Antisense Research and Applications, CRC Press, Boca Raton, 1993, pp. 276–278) and are presently preferred base substitutions, even more particularly when combined with 2'-O-methoxyethyl sugar modifications.

In one aspect of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

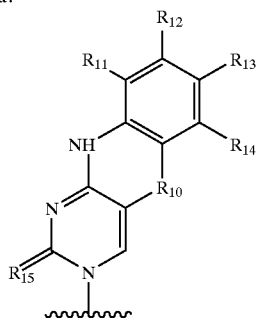

Representative cytosine analogs that make three hydrogen bonds with a guanosine in a second strand include 1,3-diazaphenoxazine-2-one ($R_{10}$=O, $R_{11}$–$R_{14}$=H) [Kurchavov, et al., Nucleosides and Nucleotides, 1997, 16, 1837–1846], 1,3-diazaphenothiazine-2-one ($R_{10}$=S, $R_{11}$–$R_{14}$=H), [Lin, K.-Y.; Jones, R. J.; Matteucci, M. J. Am. Chem. Soc. 1995, 117, 3873–3874] and 6,7,8,9-tetrafluoro-1,3-diazaphenoxazine-2-one ($R_{10}$=O, $R_{11\text{-}R14}$=F) [Wang, J.; Lin, K.-Y., Matteucci, M. Tetrahedron Lett. 1998, 39, 8385–8388]. Incorporated into oligo-nucleotides these base modifications were shown to hybridize with complementary guanine and the latter was also shown to hybridize with adenine and to enhance helical thermal stability by extended stacking interactions (also see U.S. Patent Application entitled "Modified Peptide Nucleic Acids" filed May 24, 2002, Ser. No. 10/155,920; and U.S. Patent Application entitled "Nuclease Resistant Chimeric Oligonucleotides" filed May 24, 2002, Ser. No. 10/013,295, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—($CH_2$)$_2$—$NH_2$, $R_{12\text{-}14}$=H) [Lin, K.-Y.; Matteucci, M. J. Am. Chem. Soc. 1998, 120, 8531–8532]. Binding studies demonstrated that a single incorporation could enhance the binding affinity of a model oligonucleotide to its complementary target DNA or RNA with a $\Delta T_m$ of up to 18° relative to 5-methyl cytosine (dC5$^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety.

The enhanced binding affinity of the phenoxazine derivatives together with their sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K.-Y.; Matteucci, M. J. Am. Chem. Soc. 1998, 120, 8531–8532]. The activity enhancement was even more pronounced in case of G-clamp, as a single substitution was shown to significantly improve the in vitro potency of a 20mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513–3518]. Nevertheless, to optimize oligonucleotide design and to better understand the impact of these heterocyclic modifications on the biological activity, it is important to evaluate their effect on the nuclease stability of the oligomers.

Further modified polycyclic heterocyclic compounds useful as heterocyclcic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and U.S. patent application Ser. No. 09/996,292 filed Nov. 28, 2001, certain of which are commonly owned with the instant application, and each of which is herein incorporated by reference.

The compounds described herein may have asymmetric centers. Unless otherwise indicated, all chiral, diastereomeric, and racemic forms are included in the present invention. Geometric isomers may also be present in the compounds described herein, and all such stable isomers are contemplated by the present invention. It will be appreciated that compounds in accordance with the present invention that contain asymmetrically substituted carbon atoms may be isolated in optically active or racemic forms or by synthesis.

The present invention includes all isotopes of atoms occurring in the intermediates or final compounds. Isotopes include those atoms having the same atomic number but different mass numbers. By way of example, and without limitation, isotopes of hydrogen include tritium and deuterium.

Oligomeric compounds can have a variety of substituent groups attached at various positions. Furanosyl groups found in native nucleic acids as well as various oligomeric compounds can be substituted at a number of positions. The most frequently substituted position is the 2'-position of ribose. The 3', 4', and 5' have also been substituted with substituent groups generally referred to as sugar substituent groups. Preferred sugar substituent groups include: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m CH_3$, O($CH_2$)$_n OCH_3$, O($CH_2$)$_n NH_2$, O($CH_2$)$_n CH_3$, O($CH_2$)$_n ONH_2$, and O($CH_2$)$_n ON[($CH_2$)$_n CH_3$)]$_2$, where n and m are from 1 to about 10. Other sugar substituent groups include: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties.

More preferred sugar substituent groups that are more frequently covalently attached to the 2'-sugar position include methoxyethoxy (—O—CH$_2$CH$_2$OCH$_3$, also known as —O-(2-methoxyethyl) or MOE) (Martin et al., *Helv. Chim. Acta*, 1995, 78, 486–504) i.e., an alkoxyalkoxy group. A further preferred 2'-modification includes dimethylaminooxyethoxy, i.e., a —O(CH$_2$)$_2$ON(CH$_3$)$_2$ group, also known as DMAOE, as described in examples hereinbelow, and -dimethylaminoethoxyethoxy (also known in the art as —O-dimethylaminoethoxyethyl or -DMAEOE), i.e., O—CH$_2$—O—CH$_2$—N(CH$_2$)$_2$, also described in examples hereinbelow.

Other preferred sugar substituent groups that are more frequently covalently attached to the 2'-sugar position include methoxy (—O—CH$_3$), aminopropoxy (—OCH$_2$CH$_2$CH$_2$NH$_2$), allyl (—CH$_2$—CH=CH$_2$), —O-allyl (—O—CH$_2$—CH=CH$_2$) and fluoro (—F). A 2'-substituent group on a furanosyl ring can be in the ribo (down) or arabino (up) position. Preferred 2'-arabino modifications include fluoro and hydroxy. Similar modifications may also be made at other positions on an oligomeric compound, particularly the 3' position of the sugar for a 2'-5' linked oligomeric compound, the 3'-terminus and the 5'-position of the 5'-terminus. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Further representative substituent groups include groups of formula I$_a$ or II$_a$:

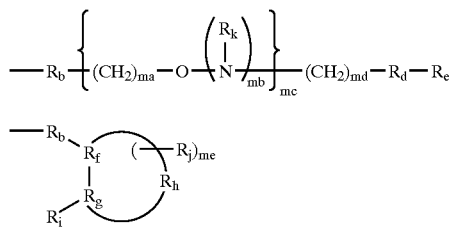

wherein:
R$_b$ is O, S or NH;
R$_d$ is a single bond, O, S or C(=O);
R$_e$ is C$_1$–C$_{10}$ alkyl, N(R$_k$)(R$_m$), N(R$_k$)(R$_n$), N=C(R$_p$)(R$_q$), N=C(R$_p$)(R$_r$) or has formula III$_a$;

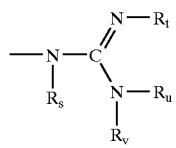

R$_p$ and R$_q$ are each independently hydrogen or C$_1$–C$_{10}$ alkyl;
R$_r$ is —R$_x$—R$_y$;
each R$_s$, R$_t$, R$_u$ and R$_v$ is, independently, hydrogen, C(O)R$_w$, substituted or unsubstituted C$_1$–C$_{10}$ alkyl, substituted or unsubstituted C$_2$–C$_{10}$ alkenyl, substituted or unsubstituted C$_2$–C$_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, R$_u$ and R$_v$, together form a phthalimido moiety with the nitrogen atom to which they are attached;
each R$_w$ is, independently, substituted or unsubstituted C$_1$–C$_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;
R$_k$ is hydrogen, a nitrogen protecting group or —R$_x$—R$_y$;
R$_p$ is hydrogen, a nitrogen protecting group or —R$_x$—R$_y$;
R$_x$ is a bond or a linking moiety;
R$_y$ is a chemical functional group, a conjugate group or a solid support medium;
each R$_m$ and R$_n$ is, independently, H, a nitrogen protecting group, substituted or unsubstituted C$_1$–C$_{10}$ alkyl, substituted or unsubstituted C$_2$–C$_{10}$ alkenyl, substituted or unsubstituted C$_2$–C$_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; NH$_3^+$, N(R$_u$)(R$_v$), guanidino and acyl where said acyl is an acid amide or an ester;
or R$_m$, and R$_n$, together, are a nitrogen protecting group, are joined in a ring structure that optionally includes an additional heteroatom selected from N and O or are a chemical functional group;
R$_1$ is OR$_z$, SR$_z$, or N(R$_z$)$_2$;
each R$_z$ is, independently, H, C$_1$–C$_8$ alkyl, C$_1$–C$_8$ haloalkyl, C(=NH)N(H)R$_u$, C(=O)N(H)R$_u$ or OC(=O)N(H)R$_u$;
R$_f$, R$_g$ and R$_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;
R$_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, N(R$_k$)(R$_m$)OR$_k$, halo, SR$_k$ or CN;
m$_a$ is 1 to about 10;
each mb is, independently, 0 or 1;
mc is 0 or an integer from 1 to 10;
md is an integer from 1 to 10;
me is from 0, 1 or 2; and
provided that when mc is 0, md is greater than 1.

Representative substituent groups of Formula I are disclosed in U.S. Pat. No. 6,172,209 entitled "Capped 2'-Oxyethoxy Oligonucleotides," hereby incorporated by reference in its entirety.

Representative cyclic substituent groups of Formula II are disclosed in U.S. Pat. No. 6,271,358 entitled "RNA Targeted 2'-Modified Oligonucleotides that are Conformationally Preorganized," hereby incorporated by reference in its entirety.

Particularly preferred sugar substituent groups include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10.

Some preferred oligomeric compounds of the invention contain, at least one nucleoside having one of the following substituent groups: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligomeric compound, or a group for improving the pharmacodynamic properties of an oligomeric compound, and other substituents having similar properties. A preferred modification includes 2'-methoxyethoxy [2'-O—CH$_2$CH$_2$OCH$_3$, also known as 2'-O-(2-methoxyethyl) or 2'-MOE](Martin et aL, Helv. Chim. Acta, 1995, 78, 486), i.e., an alkoxyalkoxy group. A further preferred modification is 2'-dimethylaminooxyethoxy, i.e., a O(CH$_2$)$_2$ON(CH$_3$)$_2$ group, also known as 2'-DMAOE. Representative aminooxy substituent groups are described in co-owned U.S. Pat. No. 6,576,752 entitled "Aminooxy-Functionalized Oligomers"; and U.S. Pat. No. 6,639,062 entitled "Aminooxy-Functionalized Oligomers and Methods for Making Same;" hereby incorporated by reference in their entirety.

Other preferred modifications include 2'-methoxy (2'-O—CH$_3$), 2'-aminopropoxy (2'-OCH$_2$CH$_2$CH$_2$NH$_2$) and 2'-fluoro (2-F). Similar modifications may also be made at other positions on nucleosides and oligomers, particularly the 3' position of the sugar on the 3' terminal nucleoside or at a 3'-position of a nucleoside that has a linkage from the 2'-position such as a 2'-5'linked oligomer and at the 5' position of a 5' terminal nucleoside. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. Pat. No. 5,859,221 also herein incorporated by reference.

Representative guanidino substituent groups that are shown in formula III and IV are disclosed in co-owned U.S. Pat. No. 6,593,466 entitled "Functionalized Oligomers", hereby incorporated by reference in its entirety.

Representative acetamido substituent groups are disclosed in U.S. Pat. No. 6,147,200 which is hereby incorporated by reference in its entirety.

Representative dimethylaminoethyloxycthyl substituent groups are disclosed in International Patent Application PCT/US99/17895, entitled "2'-O-Dimethylaminoethyloxyethyl-Modified Oligonucleotides", filed Aug. 6, 1999, hereby incorporated by reference in its entirety.

A further preferred modification of oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., Proc. Natl. Acad. Sci. USA, 1989, 86, 6553–6556), cholic acid (Manoharan et al., Bioorg. Med. Chem. Let., 1994, 4, 1053–1060), a thioether, e.g., hexyl-S-tritylthiol (Manoharan et al., Ann. N. Y. Acad. Sci., 1992, 660, 306–309; Manoharan et al., Bioorg. Med. Chem. Let., 1993, 3, 2765–2770), a thiocholesterol (Oberhauser et al., Nucl. Acids Res., 1992, 20, 533–538), an aliphatic chain, e.g., dodecandiol or undecyl residues (Saison-Behmoaras et al., EMBO J., 1991, 10, 1111–1118; Kabanov et al., FEBS Lett., 1990, 259, 327–330; Svinarchuk et al., Biochimie, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651–3654; Shea et al., Nucl. Acids Res., 1990, 18, 3777–3783), a polyamine or a polyethylene glycol chain (Manoharan et al., Nucleosides & Nucleotides, 1995, 14, 969–973), or adamantane acetic acid (Manoharan et al., Tetrahedron Lett., 1995, 36, 3651–3654), a palmityl moiety (Mishra et al., Biochim. Biophys. Acta, 1995, 1264, 229–237), or an octadecylamine or hexylamino-carbonyl-oxycholesterol moiety (Crooke et al., J. Pharmacol. Exp. Ther., 1996, 277, 923–937.

Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chiorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. No. 6,656,730 which is incorporated herein by reference in its entirety.

Representative U.S. patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given oligomeric compound to be uniformly modified, and in fact more than one of the aforementioned modifications may be incorporated in a single oligomeric compound or even at a single monomeric subunit such as a nucleoside within an oligomeric compound. The present invention also includes oligomeric compounds which are chimeric compounds. "Chimeric" oligomeric compounds or "chimeras," in the context of this invention, are oligomeric compounds which contain two or more chemically distinct regions, each made up of at least one monomer unit, i.e., a nucleotide in the case of an oligomeric compound. These oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, modified oligonucleotides, oligonucleotide analogs, oligonucleosides and/or oligonucleotide mimetics as described above. Such compounds have also been referred to in the art as hybrids hemimers, gapmers or inverted gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

In certain embodiments, the oligomeric compounds of the invention can be chimeric oligonucleotides, including "gapmers," "inverted gapmers," or "hemimers." In a "hemimer," a single terminal (either 5' or 3') region of the oligonucleotide contains modified nucleosides. When both termini of the oligonucleotide contain modified nucleosides, the oligonucleotide is called a "gapmer" and the modified 5'- and 3'-terminal regions are referred to as "wings". In a gapmer, the 5' and 3' wings can contain nucleosides modified in the same or different manner. In an "inverted gapmer" a central region of the oligonucleotide contains modified nucleosides.

As used herein, the term "oligomeric compound conjugate" refers to an oligomeric compound to which one or more chemical entities are covalently attached. In preferred embodiments of the invention, an oligomeric compound is conjugated to an amphipathic moiety. In particularly preferred embodiments of the invention, an oligomeric compound is conjugated to an α-helical, amphipathic peptide that has a hydrophobic face and a hydrophilic face.

As used herein, the term "amphipathic moiety" or "amphipathic compound" refers to any molecule, or any portion of a molecule, that contains both a hydrophilic moiety and a hydrophobic moiety.

In certain embodiments, the novel compounds of the invention comprise oligomeric compounds conjugated to one or more amphipathic moieties. In some embodiments of the invention, the one or more amphipathic moieties are amphipathic peptides.

Cationic, amphipathic peptides have been shown to have the ability to cross the plasma membrane of cells, and have been used to facilitate the uptake of a variety of biopolymers and small molecules. Wender, P. *PNAS* 2000, 97, 13003–13008; Oehlke, J. *Biochimica et Biophysica Acta* 1998, 1414, 127–139; Tossi, A. *Biopolymers (Peptide Science)* 2000, 55, 4–30; S Derossi, D. *The Journal of Biological Chemistry* 1994, 269, 10444–10450; Derossi, D. *The Journal of Biological Chemistry* 1996, 271, 18188–18193; Good, L. *Nature Biotechnology*, 2001, 19, 360–364; Pooga, M. *The FASEB Journal*; 1998, 12, 67–77; Pooga, M. *The FASEB Journal*, 2001, Express Article 10.1096/fj.00–0780fje; Vivest, E. *The Journal of Biological Chemistry*, 1997, 272, 16010–16017; Mitchell, D. *J. Pepetides Res.*, 2000, 56, 318–325; Schwarze, S. *Trends in Cell Biology*, 2000, 10, 290–295; Schwarze, S. *Science*, 1999, 285, 1569–1572.

In certain embodiments, the novel compounds of the invention comprise oligomeric compounds conjugated to amphipathic peptides of from about 8 to about 30 amino acids, wherein the amphipathic peptide has at least one hydrophobic face and at least one hydrophilic face and is capable of forming an α-helical structure. In certain preferred embodiments, the novel compounds of the invention comprise oligomeric compounds conjugated to amphipathic peptides of from about 8 to about 20 amino acids.

In certain embodiments, the novel compounds of the invention comprise oligomeric compounds conjugated to amphipathic peptides of formula II:

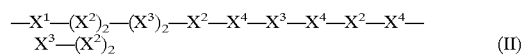
$$-X^1-(X^2)_2-(X^3)_2-X^2-X^4-X^3-X^4-X^2-X^4-X^3-(X^2)_2 \quad\quad (II)$$

wherein $X^1$ is glycine; each $X^2$ is, independently, lysine, arginine, ornithine, or homoarginine; each $X^3$ is, independently, alanine, valine, leucine, isoleucine, phenylalanine, tyrosine, tryptophan, cysteine, or methionine; and each $X^4$ is, independently, glycine, serine, threonine, aspartate, glutamate, asparagine, or glutamine.

In certain embodiments, the novel compounds of the invention comprise oligomeric compounds conjugated to one or more of the following amphipathic peptides:

| | |
|---|---|
| -GKKAFKGAGKGFKK; | (SEQ ID NO:1) |
| -GRRAFRGAGRGFRR; | (SEQ ID NO:2) |
| -GGKAFKGAGKGFKG; | (SEQ ID NO:3) |
| -GKKAFKGAGKGFKG; | (SEQ ID NO:4) |
| -GRRAFRGAGRGFRG; | (SEQ ID NO:5) |
| -GKKAFKGAGKKFKK; | (SEQ ID NO:6) |
| -GKKAFKKAKKRFKK; | (SEQ ID NO:7) |
| -GRRAFRRARRRFRR; | (SEQ ID NO:8) |
| -GKKAWKGAGKGWKK; | (SEQ ID NO:9) |
| -GRKAWKAWAKAWKK; | (SEQ ID NO:10) |
| -GKKLFKGLGKGFKK; | (SEQ ID NO:11) |
| -GKKLFKLFLKLFKK; | (SEQ ID NO:12) |
| -GKKLWKGLGKGWKK; | (SEQ ID NO:13) |
| -GKKLWKIWLKLWKK; | (SEQ ID NO:14) |
| -GKKWFKGWGKGFKK; | (SEQ ID NO:15) |
| -GKKWFKWFWKFFKK; | (SEQ ID NO:16) |

```
-GKKALKGAGKGLKK;         (SEQ ID NO:17)

-GKKALKLAAKLLKK;         (SEQ ID NO:18)

-GKKAFKQAQKQFKK;         (SEQ ID NO:19)

-GKKAFKGAEKGFKK;         (SEQ ID NO:20)

-GKKAFKEAGKGFKK;         (SEQ ID NO:21)

-GKKAFKEAEKGFKK; and     (SEQ ID NO:22)

-GKKAFKERAEKGFKK.        (SEQ ID NO:23)
```

In certain embodiments, the novel compounds of the invention comprise oligomeric compounds conjugated to one or more amphipathic peptides through a linking moiety. In one aspect of the present invention, "linking moiety" refers to a hydrocarbyl chain capable of covalently attaching an oligomeric compound to an amphipathic peptide. The linking moieties can also be used to attach targeting moieties to the peptide conjugated oligomeric compound thus formed at the amphipathic peptide or the oligomeric compound portion. Linking moieties include, but are not limited to, succinyl groups, substituted or unsubstituted $C_1$–$C_{10}$ alkyl, substituted or unsubstituted $C_2$–$C_{10}$ alkenyl or substituted or unsubstituted $C_2$–$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl and alkynyl.

In preferred embodiments of the invention, the linking moiety is a moiety of formula III:

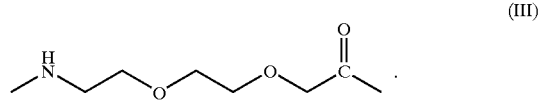

(III)

In other embodiments, the novel compounds of the invention comprise an oligomeric moiety, one or more amphipathic moieties, and one or more targeting moieties. As used herein, the term "targeting moiety" or "targeting compound" refers to any agent that directs a molecule of interest to particular cells or particular types of cells. Examples of targeting moieties include, but are not limited to, ligands that bind to cellular receptors, such as, for example, transferrin, folate, epidermal growth factor, nerve growth factor, and insulin. Targeting moieties also include, but are not limited to, alpha-fetoprotein, galactose, galactosamine, lactose, mannose, polyclonal antibodies, moloclonal antibodies, Vitamin $B_{12}$, ibuprofen, cholesterol, low-density lipoprotein, and peptides comprising an arginine-glycine-aspartic acid sequence.

In particular embodiments, an amphipathic moiety is covalently linked to the oligomeric moiety and a targeting moiety is covalently linked to the oligomeric moiety. In other embodiments of the invention, an amphipathic moiety is covalently linked to the oligomeric moiety and a targeting moiety is covalently linked to the amphipathic moiety.

Although not wishing to be bound by any theory, it is thought that conjugation of oligomeric compounds to one or more amphipathic moieties enhances the pharmacodynamic and pharmacokinetic properties of the compounds by improving the ability of the compounds to penetrate cell membranes and by improving the cellular distribution of the compounds once the compounds are inside cells. In addition, it is thought that conjugation of oligomeric compounds to one or more targeting moieties results in uptake of the oligomeric compound conjugates by specific types of cells. For example, targeting moieties can be ligands for cell surface receptors that are expressed by certain specific types of cells. Conjugation of an oligomeric compound to such a ligand and administration of the conjugate to an organism is thought to result in uptake of the conjugate by cells expressing cell surface receptors that bind the ligand.

In particular embodiments of the invention, peptide-conjugated oligomeric compounds are prepared by assembling peptides on support media and by further assembling oligomeric compounds on the support-bound peptides. In preferred embodiments of the invention, peptide-conjugated oligomeric compounds are prepared by assembling peptides on derivatized support media. In particularly preferred embodiments, the carboxy-terminal amino acid of the peptide is coupled to a detivitized support media, and coupling reactions with additional amino acids are carried according to standard procedures out until the entire peptide is synthesized. In certain embodiments of the invention, a spacer or linking group is then conjugated to the amino-terminal amino acid of the peptide. In particular embodiments of the invention, the oligomeric compound moiety is then assembled on the support-bound peptide. In preferred embodiments, the 3' nucleoside or other monomer unit of the oligomeric compound is coupled to the spacer and coupling reactions with additional nucleosides or other monomer units are carried out according to standard procedures until the entire oligomeric moiety is synthesized. In certain embodiments, the conjugate is cleaved from the solid support and purified. In preferred embodiments of the invention, the oligomeric compound-peptide conjugate is purified by HPLC.

Standard procedures for the synthesis of oligomeric compounds involve attachment of a first nucleoside or larger nucleosidic synthon to support media followed by iterative elongation of the nucleoside or nucleosidic synthon to yield a final oligomeric compound. In some embodiments of the invention, oligomeric compounds are synthesized by attaching a 5'-O-protected nucleoside to a derivatized solid support, deprotecting the 5'-hydroxyl of the nucleoside with a deprotecting reagent, reacting the deprotected 5'-hydroxyl with a 5'-protected activated phosphorus compound to produce a covalent linkage therebetween, oxidizing or sulfurizing the covalent linkage, and repeating the deprotecting, reacting, and oxidizing steps to produce an oligomer attached to the derivatized support media.

Support media can be selected to be insoluble or to have variable solubility in different solvents, which allows the growing oligomer to be kept out of or in solution as desired. Traditional solid supports are insoluble, while soluble supports have recently been introduced. Soluble polymer supports allow the bound oligomer to be precipitated or dissolved at desired points in the synthesis (Gravert et al., Chem. Rev., 1997, 97, 489–510).

Representative support media amenable to the present invention include, without limitation, controlled pore glass (CPG); oxalyl-controlled pore glass (see, e.g., Alul, et al., Nucleic Acids Research 1991, 19, 1527); TENTAGEL Support, (see, e.g., Wright, et al., Tetrahedron Letters 1993, 34, 3373); and POROS, a copolymer of polystyrene/divinylbenzene available from Perceptive Biosystems. Use of poly(ethylene glycol) of molecular weight between 5 and 20 kDa as a soluble support media for large-scale synthesis of phosphorothioate oligonucleotides is described in Bonora et al., Organic Process Research & Development, 2000, 4, 225–231. Equipment for such synthesis is sold by several vendors including, for example, Applied Biosystems (Foster City, Calif.).

Other means for synthesis of oligomeric compounds may additionally or alternatively be employed. Techniques for synthesizing oligonucleotides, such as phosphorothioates and alkylated derivatives, are familiar to those of ordinary skill in the art.

Activated phosphorus compositions (e.g. compounds having activated phosphorus-containing substituent groups) may be used in coupling reactions for the synthesis of oligomeric compounds. As used herein, the term "activated phosphorus composition" includes monomers and oligomers that have an activated phosphorus-containing substituent group that reacts with a hydroxyl group of another monomeric or oligomeric compound to form a phosphorus-containing internucleotide linkage. Such activated phosphorus groups contain activated phosphorus atoms in $P^{III}$ valence state. Such activated phosphorus atoms are known in the art and include, but are not limited to, phosphoramidite, H-phosphonate, phosphate triesters and chiral auxiliaries. A preferred synthetic solid phase synthesis utilizes phosphoramidites as activated phosphates. The phosphoramidites utilize $P^{III}$ chemistry. The intermediate phosphite compounds are subsequently oxidized to the $P^V$ state using known methods to yield, in a preferred embodiment, phosphodiester or phosphorothioate internucleotide linkages. Additional activated phosphates and phosphites are disclosed in Tetrahedron Report Number 309 (Beaucage and Iyer, *Tetrahedron*, 1992, 48, 2223–2311).

A representative list of activated phosphorus-containing monomers or oligomers include those having the formula:

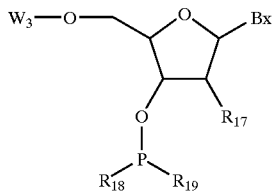

wherein each Bx is, independently, a heterocyclic base moiety or a blocked heterocyclic base moiety; and each $R_{17}$ is, independently, H, a blocked hydroxyl group, a sugar substituent group, or a blocked substituent group;

$W_3$ is an hydroxyl protecting group, a nucleoside, a nucleotide, an oligonucleoside or an oligonucleotide;

$R_{18}$ is $N(L_1)L_2$;

each $L_1$ and $L_2$ is, independently, $C_{1-6}$ alkyl;

or $L_1$ and $L_2$ are joined together to form a 4- to 7-membered heterocyclic ring system including the nitrogen atom to which $L_1$ and $L_2$ are attached, wherein said ring system optionally includes at least one additional heteroatom selected from O, N and S; and $R_{19}$ is $X_1$;

$X_1$ is Pg—O—, Pg—S—, $C_1$–$C_{10}$ straight or branched chain alkyl, $CH_3(CH_2)_{p5}$—O— or $R_{20}R_{21}N$—;

p5 is from 0 to 10;

Pg is a protecting group;

each $R_{20}$ and $R_{21}$ is, independently, hydrogen, $C_1$–$C_{10}$ alkyl, cycloalkyl or aryl;

or optionally, $R_{20}$ and $R_{21}$, together with the nitrogen atom to which they are attached form a cyclic moiety that may include an additional heteroatom selected from O, S and N; or $R_{18}$ and $R_{19}$ together with the phosphorus atom to which $R_{18}$ and $R_{19}$ are attached form a chiral auxiliary.

Groups attached to the phosphorus atom of internucleotide linkages before and after oxidation ($R_{18}$ and $R_{19}$) can include nitrogen containing cyclic moieties such as morpholine. Such oxidized internucleoside linkages include a phosphoromorpholidothioate linkage (Wilk et al., *Nucleosides and nucleotides*, 1991, 10, 319–322). Further cyclic moieties amenable to the present invention include mono-, bi- or tricyclic ring moieties that may be substituted with groups such as oxo, acyl, alkoxy, alkoxycarbonyl, alkyl, alkenyl, alkynyl, amino, amido, azido, aryl, heteroaryl, carboxylic acid, cyano, guanidino, halo, haloalkyl, haloalkoxy, hydrazino, ODMT, alkylsulfonyl, nitro, sulfide, sulfone, sulfonamide, thiol and thioalkoxy. A preferred bicyclic ring structure that includes nitrogen is phthalimido.

In the context of this specification, alkyl (generally C1–C20), alkenyl (generally C2–C20), and alkynyl (generally C2–C20) groups include, but are not limited to, substituted and unsubstituted straight chain, branch chain, and alicyclic hydrocarbons, including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon alkyl groups. Further examples include 2-methylpropyl, 2-methyl-4-ethylbutyl, 2,4-diethylbutyl, 3-propylbutyl, 2,8-dibutyldecyl, 6,6-dimethyl-octyl, 6-propyl-6-butyloctyl, 2-methylbutyl, 2-methylpentyl, 3-methylpentyl, 2-ethylhexyl and other branched chain groups, allyl, crotyl, propargyl, 2-pentenyl and other unsaturated groups containing a pi bond, cyclohexane, cyclopentane, adamantane as well as other alicyclic groups, 3-penten-2-one, 3-methyl-2-butanol, 2-cyanooctyl, 3-methoxy-4-heptanal, 3-nitrobutyl, 4-isopropoxydodecyl, 4-azido-2-nitrodecyl, 5-mercaptononyl, 4-amino-1-pentenyl as well as other substituted groups. Representative alkyl substituents are disclosed in U.S. Pat. No. 5,212,295, at column 12, lines 41–50, hereby incorporated by reference in its entirety.

A number of chemical functional groups can be introduced into compounds of the invention in a blocked form and subsequently deblocked to form a final, desired compound. Such groups can be directly or indirectly attached at the heterocyclic bases, the internucleoside linkages and the sugar substituent groups at one or more of the 2', 3' and 5'-positions. Protecting groups can be selected to block functional groups located in a growing oligomeric compound during iterative oligonucleotide synthesis while other positions can be selectively deblocked as needed. In general, a blocking group renders a chemical functionality of a larger molecule inert to specific reaction conditions and can later be removed from such functionality without substantially damaging the remainder of the molecule (Greene and Wuts, Protective Groups in Organic Synthesis, 3rd ed, John Wiley & Sons, New York, 1999). For example, the nitrogen atom of amino groups can be blocked as phthalimido groups, as 9-fluorenylmethoxycarbonyl (FMOC) groups, and with triphenylmethylsulfenyl, t-BOC or benzyl groups. Carboxyl groups can be blocked as acetyl groups. Representative hydroxyl protecting groups are described by Beaucage et al., Tetrahedron 1992, 48, 2223. Preferred hydroxyl protecting groups are acid-labile, such as the trityl, monomethoxytrityl, dimethoxytrityl, trimethoxytrityl, 9-phenylxanthine-9-yl (Pixyl) and 9-(p-methoxyphenyl)xanthine-9-yl (MOX).

Chemical functional groups can also be "blocked" by including them in a precursor form. Thus, an azido group can be considered a "blocked" form of an amine since the azido group is easily converted to the amine. Further representative protecting groups utilized in oligonucleotide synthesis are discussed in Agrawal, et al., Protocols for Oligonucleotide Conjugates, Eds, Humana Press; New Jersey, 1994; Vol. 26 pp. 1–72.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p=-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Examples of thiol (sulfur) protecting groups include, but are not limited to, benzyl, substituted benzyls, diphenylmethly, phenyl, t-butyl, methoxymethyl, thiazolidines, acetyl and benzoyl. Further thiol protecting groups are illustrated in Greene and Wuts, ibid.

Additional amino-protecting groups include but are not limited to, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl. Equivalents of these amino-protecting groups are also encompassed by the compounds and methods of the present invention.

Some preferred amino-protecting groups are stable to acid treatment and can be selectively removed with base treatment, which makes reactive amino groups selectively available for substitution. Examples of such groups are the Fmoc (E. Atherton and R. C. Sheppard in The Peptides, S. Udenfriend, J. Meienhofer, Eds., Academic Press, Orlando, 1987, volume 9, p.1), and various substituted sulfonylethyl carbamates exemplified by the Nsc group (Samukov et al., Tetrahedron Lett, 1994, 35:7821; Verhart and Tesser, Rec. Trav. Chim. Pays-Bas, 1987, 107:621).

In some especially preferred embodiments, the nucleoside components of the oligomeric compounds are connected to each other by optionally protected phosphorothioate internucleoside linkages. Representative protecting groups for phosphorus containing internucleoside linkages such as phosphite, phosphodiester and phosphorothioate linages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. No. 4,725,677 and Re. 34,069 (β-cyanoethyl); Beaucage, S. L. and Iyer, R. P., Tetrahedron, 49 No. 10, pp. 1925–1963 (1993); Beaucage, S. L. and Iyer, R. P., Tetrahedron, 49 No. 46, pp. 10441–10488 (1993); Beaucage, S. L. and Iyer, R. P., Tetrahedron, 48 No. 12, pp.

The oligomeric compound conjugates in accordance with the invention can be used in diagnostics, therapeutics and as research reagents and kits. The compounds can be used in pharmaceutical compositions by including a suitable pharmaceutically acceptable diluent or carrier. They can further be used for treating organisms having a disease characterized by the undesired production of a protein. The organism should be contacted with an oligomeric compound conjugate having an oligonucleotide sequence that is capable of specifically hybridizing with a strand of nucleic acid encoding the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, plants and higher animal forms, including warm-blooded animals, can be treated. Further, each cell of multicellular eukaryotes can be treated, as such cells carry out both DNA-RNA transcription and RNA-protein translation as integral parts of their activity. Furthermore, many of the organelles (e.g., mitochondria and chloroplasts) of eukaryotic cells also include transcription and translation mechanisms. Thus, single cells, cellular populations, or organelles can also be included within the definition of organisms that can be treated with therapeutic or diagnostic oligonucleotides.

For therapeutics, an animal, preferably a human, suspected of having a disease or disorder which can be treated by modulating the expression of a particular target gene is treated by administering oligomeric compound conjugates in accordance with this invention. The oligomeric compound conjugates of the invention can be utilized in pharmaceutical compositions by adding an effective amount of the oligomeric compound conjugates to a suitable pharmaceutically acceptable diluent or carrier. Use of the oligomeric compound conjugates and methods of the invention may also be useful prophylactically, e.g., to prevent or delay infection, inflammation or tumor formation, for example.

The oligomeric compound conjugates of the invention are useful for research and diagnostics, because these compounds can be prepared to hybridize to nucleic acids encoding a particular protein, enabling sandwich and other assays to easily be constructed to exploit this fact. Hybridization of the oligomeric compound conjugates of the invention with a nucleic acid encoding a particular protein can be detected by means known in the art. Such means may include conjugation of an enzyme to an oligomeric compound conjugate, radiolabelling of the oligomeric compound conjugate, or any other suitable detection means. Kits using such detection means for detecting protein levels in a sample may also be prepared.

The methods of the invention can be used in connection with diagnostics and therapeutics. Methods in accordance with the invention can be used to improve the permeation of biological membranes by therapeutic and diagnostic oligomeric compounds. Further, the methods of the invention can be used to improve the cellular distribution of therapeutic and diagnostic oligomeric compound conjugates once the compounds penetrate biological membranes.

The present invention also includes pharmaceutical compositions and formulations that include the oligomeric compound conjugates of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligomeric compound conjugates of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligomeric compound conjugates of the invention may be encapsulated within liposomes or may form complexes thereto, in particular to cationic liposomes. Alternatively, oligomeric compound conjugates may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcamitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligomeric compound conjugates of the invention are administered in conjunction with one or more penetration enhancers, surfactants, and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium).

Also preferred are combinations of penetration enhancers, for example, fatty acids/salts in combination with bile acids/salts. A particularly preferred combination is the sodium salt of laurie acid, capric acid and UDCA. Further penetration enhancers include polyoxyethylene-9-lauryl ether, polyoxyethylene-20-cetyl ether. Oligomeric compound conjugates of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcyanoacrylate), DEAE-methacrylate, DEAE-hexylacrylate, DEAE-acrylamide, DEAE-albumin and DEAE-dextran, polymethylacrylate, polyhexylacrylate, poly(D,L-lactio acid), poly(DL-lactic-co-glycolic acid (PLGA), alginate, and polyethyleneglycol (PEG). Oral formulations for oligonucleotides and their preparation are described in detail in U.S. applications Ser. No. 08/886,829 (filed Jul. 1, 1997, now abandoned), Ser. No. 09/108,673 (filed Jul. 1, 1998), Ser. No. 09/256,515 (filed Feb. 23, 1999, now abandoned), Ser. No. 09/082,624 (filed May 21, 1998, now abandoned) and Ser. No. 09/315,298 (filed May 20, 1999) each of which is incorporated herein by reference in its entirety.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension can also contain stabilizers.

In one embodiment of the present invention, the pharmaceutical compositions are formulated and used as foams. Pharmaceutical foams include formulations such as, but not limited to, emulsions, microemulsions, creams, jellies and liposomes. While basically similar in nature, these formulations vary in the components and the consistency of the final product. The preparation of such compositions and formulations is generally known to those skilled in the pharmaceutical and formulation arts and may be applied to the formulation of the compositions of the present invention.

The compositions of the present invention can be prepared and formulated as emulsions. Emulsions are typically heterogenous systems of one liquid dispersed in another in the form of droplets usually exceeding 0.1 μm in diameter. (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions can contain components in addition to the dispersed phases, and the active drug can be present as a solution in either the aqueous phase, oily phase or as a separate phase. Pharmaceutical excipients such as emulsifiers, stabilizers, dyes, and anti-oxidants can also be present in emulsions. Pharmaceutical emulsions can also comprise more than two phases, such as, for example oil-in-water-in-oil (o/w/o) and water-in-oil-in-water (w/o/w) emulsions. Such complex formulations often provide advantages that are not achieved with simple binary emulsions. Multiple emulsions in which individual oil droplets of an o/w emulsion enclose small water droplets constitute a w/o/w emulsion. Likewise, a system of oil droplets enclosed in globules of water stabilized in an oily continuous provides an o/w/o emulsion.

Emulsions are characterized by little or no thermodynamic stability. Often, the dispersed or discontinuous phase of the emulsion is dispersed into the external or continuous phase and maintained in this form through the action of emulsifiers or the viscosity of the formulation. Either phase of the emulsion can be a semisolid or a solid, as is the case with emulsion-style ointment bases and creams. Other means of stabilizing emulsions entail the use of emulsifiers that can be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants for the preparation of formulations. Surfactants may be classified based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases, such as anhydrous lanolin and hydrophilic petrolatum, can soak up water to form w/o emulsions, yet retain their semisolid consistencies. Finely divided solids have also been used as emulsifiers, especially in combination with surfactants and in viscous preparations. Such solids include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. Such materials include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). Hydrocolloids disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, emulsion formulations often incorporate preservatives. Preservatives commonly added to emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants can be free radical scavengers such as tocopherols, alkyl gallates, butylated hydroxyanisole, butylated hydroxytoluene, or reducing agents, such as ascorbic acid and sodium metabisulfite, and antioxidant synergists such as citric acid, tartaric acid, and lecithin.

The application of emulsion formulations via dermatological, oral and parenteral routes, and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation and efficacy from an absorption and bioavailability standpoint. (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligomeric compound conjugates are formulated as microemulsions. A microemulsion may be defined as a system of water, oil and amphiphile that is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), and decaglycerol decaoleate (DAO750), alone or in combination with cosurfactants. The cosurfactant, usually a short-chain alcohol such as ethanol, 1-propanol, or 1-butanol, serves to increase the interfacial fluidity by penetrating the surfactant film and creating a disordered film that results from the void space generated among surfactant molecules. Microemulsions can, however, be prepared without the use of cosurfactants, and alcohol-free self-emulsifying microemulsion systems are known in the art. The aqueous phase can include, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are of particular interest from the standpoint of drug solubilization and the enhanced absorption of drugs. It has been proposed that lipid based microemulsions (both o/w and w/o) enhance the oral bioavailability of drugs, including peptides (Constantinides et al., Pharmaceutical Research, 1994, 11, 1385–1390; Ritschel, Meth. Find. Exp. Clin. Pharmacol., 1993, 13, 205). Microemulsions afford improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138–143). Microemulsions often form spontaneously when their components are brought together at ambient temperature, which may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligomeric compound conjugates from the gastrointestinal tract, as well as improve the local cellular uptake of oligomeric compound conjugates within the gastrointestinal tract, vagina, buccal cavity and other areas of administration.

Microemulsions of the present invention may also contain additional components and additives such as sorbitan monostearate (Grill 3), Labrasol, and penetration enhancers that improve the properties of the formulation and enhance the absorption of the oligomeric compound conjugates of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Many organized surfactant structures other than microemulsions exist and have been studied and used for the formulation of drugs. Such structures include monolayers, micelles, bilayers and vesicles. Vesicles, such as liposomes, have attracted great interest due to their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles that have a membrane formed from a lipophilic material and an aqueous interior. The aqueous portion contains the composition to be delivered. Cationic liposomes can fuse to the cell wall. Non-cationic liposomes, although not able to fuse as efficiently with the cell wall, are taken up by macrophages in vivo. In order to cross intact mammalian skin, lipid vesicles must pass through a series of fine pores, each with a diameter less than 50 nm, under the influence of a suitable transdermal gradient. Therefore, it is desirable to use a liposome that is highly deformable and able to pass through such fine pores.

Further advantages of liposomes include biocompatability and biodegradability, the ability to incorporate a wide range of water and lipid soluble drugs, and the ability to protect encapsulated drugs from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size, and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as a mode of delivery for many drugs. Growing evidence indicates that liposomes present several advantages relative to other formulations for topical administration. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes that interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980–985).

Liposomes that are pH-sensitive or negatively-charged entrap DNA, rather than forming a complex with DNA. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269–274).

One type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., Journal of Drug Targeting, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P.Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765). Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{12}15G$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates that are attractive candidates for drug delivery vehicles. Transfersomes may be described as lipid droplets that are so highly deformable that they are easily able to penetrate through pores that are smaller than the droplet. Transfersomes are adaptable to the environment in which they are used, e.g. they are self-optimizing (adaptive to the shape of pores in the skin), self-repairing, frequently reach their targets without fragmenting, and are often self-loading. To make transfersomes, surface edge-activators, usually surfactants, are added to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide pH range. In general the HLB values of non-ionic surfactants range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides. The use of surfactants in drug products, formulations and in emulsions has been reviewed (Rieger, in Pharmaceutical Dosage Forms, Marcel Dekker, Inc., New York, N.Y., 1988, p. 285).

In one embodiment, the present invention employs various penetration enhancers to effect the efficient delivery of nucleic acids, particularly oligomeric compound conjugates, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p.92). Each of the above mentioned classes of penetration enhancers are described below in greater detail.

In connection with the present invention, surfactants (or "surface-active agents") are chemical entities which, when dissolved in an aqueous solution, reduce the surface tension of the solution or the interfacial tension between the aqueous solution and another liquid, with the result that absorption of oligomeric compound conjugates through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p.92); and perfluorochemical emulsions, such as FC-43. Takahashi et al., J. Pharm. Pharmacol., 1988, 40, 252).

Various fatty acids and their derivatives that act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcamitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carrier Systems, 1991, p.92; Muranishi, Critical Reviews in Therapeutic Drug Carrier Systems, 1990, 7, 1–33; El Hariri et al., J. Pharm. Pharmacol., 1992, 44, 651–654).

The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782–783; Muranishi, Critical Reviews in Therapeutic Drug Carrier Systems, 1990, 7, 1–33; Yamamoto et al., J. Pharm. Exp. Ther., 1992, 263, 25; Yamashita et al., J. Pharm. Sci., 1990, 79, 579–583).

Chelating agents, as used in connection with the present invention, can be defined as compounds that remove metallic ions from solution by forming complexes therewith, with the result that absorption of oligonucleotides through the mucosa is enhanced. With regard to the use of chelating agents as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315–339). Chelating agents of the invention include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., Critical Reviews in Therapeutic Drug Carrier Systems, 1991, page 92; Muranishi, Critical Reviews in Therapeutic Drug Carrier Systems, 1990, 7, 1–33; Buur et al., J. Control Rel., 1990, 14, 43–51).

As used herein, non-chelating, non-surfactant penetration enhancing compounds can be defined as compounds that demonstrate insignificant activity as chelating agents or as surfactants, but that nonetheless enhance absorption of oligomeric compound conjugates through the alimentary mucosa (Muranishi, Critical Reviews in Therapeutic Drug Carrier Systems, 1990, 7, 1–33). This class of penetration enhancers include, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621–626).

Agents that enhance uptake of oligomeric compound conjugates at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligomeric compounds.

Other agents may be utilized to enhance the penetration of the administered oligomeric compound conjugates, including glycols such as ethylene glycol and propylene glycol, pyrrols such as 2-pyrrol, azones, and terpenes such as limonene and menthone.

Certain compositions of the present invention also incorporate carrier compounds in the formulation. As used herein, "carrier compound" or "carrier" can refer to a nucleic acid, or analog thereof, that is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of an oligomeric compound conjugate and a carrier compound, typically with an excess of the latter substance, can result in a substantial reduction of the amount of oligomeric compound conjugate recovered in the liver, kidney or other extracirculatory reservoirs, presumably due to competition between the carrier compound and the oligomeric compound conjugate for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., Antisense Res. Dev., 1995, 5, 115–121; Takakura et al., Antisense & Nucl. Acid Drug Dev., 1996, 6, 177–183).

In contrast to a carrier compound, a "pharmaceutical carrier" or "excipient" is a pharmaceutically acceptable solvent, suspending agent or any other pharmacologically inert vehicle for delivering one or more oligomeric compound conjugates to an animal. The excipient may be liquid or solid and is selected, with the planned manner of administration in mind, so as to provide for the desired bulk, consistency, etc., when combined with an oligomeric compound conjugate and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with oligomeric compound conjugates can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of oligomeric compound conjugates may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration that do not deleteriously react with oligomeric compound conjugates can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligomeric compound conjugates of the formulation.

Aqueous suspensions may contain substances that increase the viscosity of the suspension including, for example, sodium carboxymethylcellulose, sorbitol and/or dextran. The suspension may also contain stabilizers.

The compounds of the invention may also be admixed, encapsulated, conjugated or otherwise associated with other molecules, molecule structures or mixtures of compounds, such as, for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Certain embodiments of the invention provide pharmaceutical compositions containing (a) one or more oligomeric compound conjugates and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the oligomeric compound conjugates of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more oligomeric compound conjugates targeted to a first nucleic acid and one or more additional oligomeric compound conjugates targeted to a second nucleic acid target. The two or more combined oligomeric compound conjugates may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

The oligomeric compound conjugates of the invention encompass pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes pharmaceutically acceptable salt of an acid form of one of the components of the compositions of the invention. Such salts include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids. Such inorganic acids include, for example, hydrobromic acid, sulfuric acid or phosphoric acid. Such organic acids include, for example, carboxylic, sulfonic, sulfo or phospho acids or N-substituted sulfamic acids, such as, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and amino acids, such as the 20 alpha-amino acids involved in the synthesis of proteins in nature, such as, for example, glutamic acid or aspartic acid, and also phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

Preferred examples of pharmaceutically acceptable salts for oligomeric compound conjugates include, but are not limited to, (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The materials, methods, and examples presented herein are intended to be illustrative, and are not intended to limit the scope of the invention. All publications, patent applications, patents, and other references mentioned herein are incorporated by reference in their entirety. Unless otherwise defined, all technical and scientific terms are intended to have their art-recognized meanings.

EXAMPLES

The following abbreviations are used throughout the Examples. The associated meaning of each abbreviation is indicated. Bhoc, benzhydryloxycarbonyl; Boc, t-butyloxycarbonyl; t-Bu, tert.-butyl; Cbz, benzyloxycarbonyl; DCM, dichloromethane; DIEA, N,N-diisopropylamine; DMF, dimethylformamide; DMT, 4,4'-dimethoxytrityl; DMS, dimethylsulfide; ESI-MS, electrospray ionization mass spectrometry; Fmoc, 9-fluorenylmethoxycarbonyl; HATU, O-(7-azabenzotriazol-1-yl)-1,1,3,3-tetramethyluronium hexafluorophosphate; HBTU, 2(1H-benzotriazole-1-yl)-1,1,3,3 -tetramethyluronium hexafluorophosphate; HMBA, 4-hydroxymethylbenzoic acid; HOBt, N-hydroxybenzotriazole; 2'-O—MOE, 2'-O-methoxyethyl; MBHA, p-methylbenzhydrylamine; NMP, N-methylpyrrolidinone; OrG488, OregonGreen 488; PNA, peptide nucleic acid; 6-ROX, 6-carboxy-X-rhodamine; RP-HPLC, reversed phase high performance liquid chromatography; TEA, triethylamine; TFA, trifluoroacetic acid; TFMSA, trifluoromethanesulfonic acid; THF, tetrahydrofuran; TIS, triisoproylsilane; Ttr, trityl; XAL, 9-aminoxanthen-3-yloxy.

The reagents and solvents used in the experiments described in the Examples were obtained as follows. The solvents used were purchased from Aldrich or J. T. Baker in the highest grade available. Amino acids, resins used for solid phase synthesis, HBTU, and HOBt were purchased from Novabiochem. Amino-functionalized macroporous PS resin was obtained from Amersham Pharmacia. PNA monomers (Fmoc and Boc-protected), HATU, and all the reagents used for oligonucleotide synthesis were obtained from Applied Biosystems. 2'-MOE phosphoramidites were synthesized in house. The fluorescent dyes 6-ROX and OrG488 were purchased from Molecular Probes. All other reagents were purchased from Sigma-Aldrich.

Example 1

Solid Phase Synthesis of PNA-Peptide Conjugates

Method 1: The peptide part of the conjugates was synthesized first by solid phase synthesis using Fmoc-chemistry and Fmoc-XAL-PEG-PS (Sieber resin, Novabiochem). The synthesis was carried out manually in 100 µmole scale in special fabricated glass columns. The PNA part of the conjugates was assembled by solid phase synthesis on the N-terminal amino group of the peptide chain after introducing a spacer molecule (O-spacer). The synthesis was carried out either using an Applied Biosystems 394 DNA/RNA Synthesizer according to the manufacturer's protocols for Fmoc PNA synthesis, which were adapted to the specific synthesis procedures used or by manual synthesis using special fabricated glass columns and Fmoc PNA chemistry. Deprotection and cleavage of the conjugates was carried out using a mixture of TFA/m-cresol/TIS/$H_2O$ (94:2.5:1:2.5), which was added to the resin and the suspension was shaken for 15 min. Then the resin was filtered off and the filtrate was allowed to stand for another 3–6 h. The filtrate was then added to a 10-fold volume of cold ether, mixed and centrifuged. The supernatant was removed and the pellet was resuspended in ether. This was repeated three times. The pellet was dried and re-dissolved in water or 0.1% TFA for HPLC purification.

Method 2: First, the PNA part of the conjugates is assembled on MBHA polystyrene resin, pre-loaded with either the first PNA building block or an amino acid commonly used for C-terminal modification of PNA (e.g. Gly, Lys, β-Ala etc.). The synthesis is carried out either manually in special fabricated glass columns or using an Applied Biosystems 433 A Peptide Synthesizer according to previously published procedures for PNA synthesis (Boc chemistry), such as those described in L. Christensen, et al. (1995), *J. Pept. Sci.* 1, 175–183; T. Koch, et al. (1997), *J. Pept. Res.* 49, 80–88. The synthesis of the peptide part of the conjugate is carried out either by using Fmoc- or Boc- chemistry, generally after introducing a linker unit, such as the O-spacer. For Deprotection and cleavage one vol. of a solution of TFA/DMS/m-cresol (1:3:1) is mixed with one vol. of TFA/TFMSA (9:1) and added to the resin. After 1 h of shaking the resin is washed with TFA and one vol. of TFA/TFMSA/m-cresol (8:2:1) is added and the suspension is shaken for another 1.5 h. The filtrate is then added to a 10-fold volume of cold ether, mixed and centrifuged. The supernatant is removed and the pellet is resuspended in ether. This is repeated three times. The pellet is dried and re-dissolved in water or 0.1% TFA for HPLC purification.

Example 2

Solid Phase Synthesis of Oligonucleotide-2'-/3'-Peptide Conjugates

For synthesis of oligonucleotide-2' or 3'-peptide conjugates, first the peptide part is synthesized either manually or by automated solid phase synthesis using standard Boc-chemistry for peptide synthesis and amino acids, which are suitable for the synthesis of oligonucleotide conjugates (s. following list). Then, the oligonucleotide part of the conjugate is synthesized by solid phase synthesis onto the N-terminus of the peptide chain after introduction of a DMT-protected spacer (e.g. DMT-O-γ-hydroxybutyric acid). Deprotection and cleavage of the conjugates is generally performed under basic conditions (e.g. aqueous $NH_3$), which requires a base-labile linker to the resin, such as a thioester or HMBA. The preparation of appropriate resins is described in Examples 6 and 7. After deprotection, the basic solution is evaporated and the conjugate is dissolved in water for HPLC purification.

Commercially available amino acids suitable for the synthesis of oligonucleotide-peptide conjugates are: Boc-Ala-OH, Boc-Cys(Acm)-OH, Boc-Gly-OH, Boc-Glu(t-Bu)-OH, Boc-Asp(t-Bu)-OH, Boc-His(Boc)-OH, Boc-Ile-OH, Boc-Leu-OH, BocLys(Fmoc)-OH, Boc-Met-OH, Boc-Orn (Fmoc)-OH→Arg by postsynthetic guanidinylation, Boc-Phe-OH, Boc-Pro-OH, Boc-Ser(t-Bu)-OH, Boc-Thr(t-Bu)-OH, Boc-Trp(For)-OH, Boc-Tyr(t-Bu)-OH, Boc-Val-OH.

Example 3

Solution Phase Synthesis of Oligonucleotide-5'-Peptide Conjugates

For synthesis of oligonucleotide-5'-peptide conjugates, the oligonucleotide and the peptide part are synthesized and purified separately following standard synthesis procedures of phosphoramidite and Fmoc- or Boc-chemistry, respectively. The conjugation is carried out in aqueous solution using functionalities on each strand, which are capable of forming a specific covalent linkage with their counterpart on the other strand in aqueous solution. Scheme 1 shows some examples of existing methods for covalent conjugation in solution.

Scheme 1.

Examples for solution phase conjugation of oligonucleotides and peptides

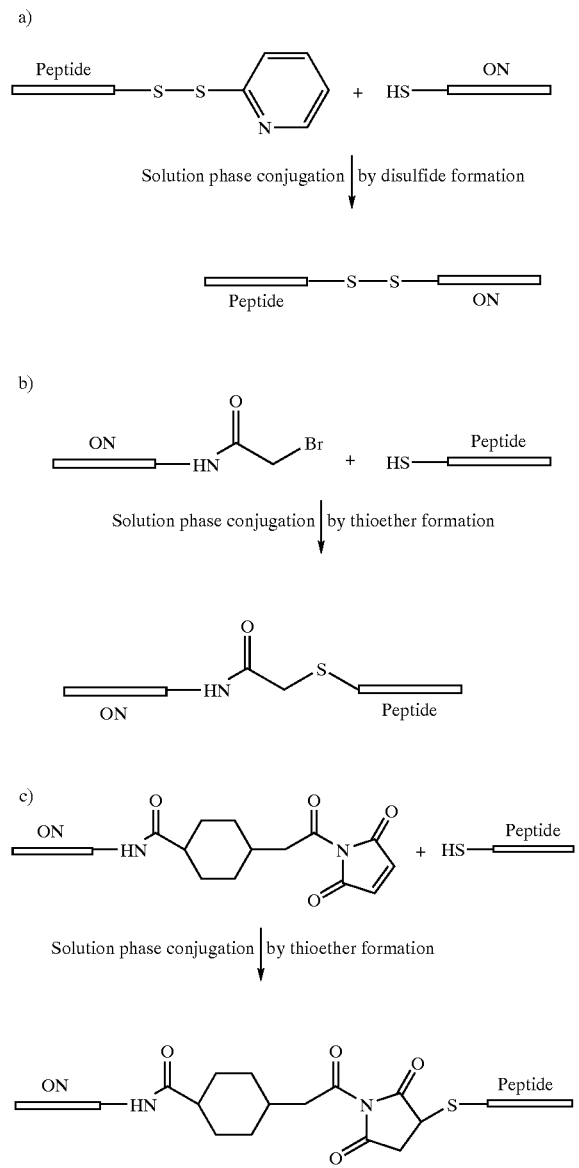

Example 4

HPLC Purification of PNA Conjugates

The conjugates were purified by RP-HPLC using a 306 Piston Pump System, an 811C Dynamic Mixer, a 70 Diode Array Detector and a 215 Liquid Handler together with the Unipoint Software (Gilson) and Jupiter (Phenomenex) or Zorbax (Hewlett Packard), $C_{18}$, 300 Å columns. 0.1% TFA in $H_2O$ (A) and $CH_3CN$ (B) were used as the solvent system. The applied gradient was dependent on the length and sequence of the conjugate. Dual wavelength detection was carried out at 220 and 260 run and the column temperature was kept between room temperature and 60° C. depending on the tendency of the conjugates for secondary structure formation.

Example 5

HPLC Purification of Oligonucleotide Conjugates

The conjugates are purified by RP-HPLC using a 306 Piston Pump System, an 811C Dynamic Mixer, a 70 Diode Array Detector and a 215 Liquid Handler together with the Unipoint Software (Gilson). The columns used, the applied solvent system, and gradient are dependent on the length and sequence of the conjugate. Dual wavelength detection is carried out at 220 and 260 mn.

Example 6

Loading of Amino-functionalized PS Resin (Macroporous) with HMBA

One g of amino-functionalized macroporous PS resin is placed in a custom fabricated glass column and the resin is washed 2× with DMF. The resin is suspended in NMP and 10 equiv. of HMBA relative to the resin loading are dissolved in NMP and 10 equiv. HATU are added followed by 60 equiv. DIEA. After 3 min of pre-activation, the activated HMBA is added to the resin by shaking the suspension. After shaking the suspension at room temperature for another 2 h, the resin is treated with aqueous $NH_3$ to cleave any unwanted ester linkages and washed with DMF and DCM. The loading of the resin with HMBA is confirmed qualitatively by Kaisertest. Any unreacted amino groups are capped by shaking the resin in 10 mL of $Ac_2O$/pyridine/NMP (1:2:2) for 1 h. Completion of capping is confirmed by Kaisertest and the resin is washed with DMF followed by DCM and dried in vacuo overnight.

Example 7

Loading of HMBA-PS Resin (Macroporous) with the C-terminal Amino Acid

One g of the HMBA-PS (macroporous) resin is placed in a custom fabricated glass column and the resin is washed 2× with DMF. The resin is suspended in DMF. Ten equiv. (rel. to the resin loading) of the first amino acid of the sequence are dissolved in DCM and a solution of 5 equiv. DIC in DCM is added. The mixture is stirred in an ice bath for 20 min, then DMF is added to dissolve the formed anhydride and mixture is stirred at room temperature for another 10 min. The anhydride solution is added to the resin followed by a solution of 1 equiv. DMAP in DMF. After shaking the suspension at room temperature for 3–12 h, the resin is washed with DMF and DCM and unreacted amino groups are capped by shaking the resin in 10 mL of $Ac_2O$/pyridine/ NMP (1:2:2) for 1 h. Completion of capping is confirmed by Kaisertest and the resin is washed with DMF followed by DCM and dried in vacuo overnight. Using a small portion of the resin, FmocGly is coupled to the amino group of the C-terminal amino acid after removal of its Boc group. Then, the loading of the resin is determined spectrophotometrically measuring the absorbance of fluoren at 302 nm after cleaving Fmoc with 20% piperidine in DMF.

Example 8

Synthesis and Characterization of the Unlabeled Peptides (aHP-1-29)

0.6 g of Fmoc-XAL-PEG-PS resin (Sieber resin, NovaBiochem, loading 0.17 mmol/g) was placed in a special fabricated glass column equipped with a glass fritt, a stop-cocked outlet and an argon inlet. The resin was washed with DMF and allowed to swell in DCM for 15 min, before the Fmoc group was removed by adding 20% piperidine in DMF and shaking the suspension for 4 min. This procedure was repeated twice. The resin was washed with DMF and the first amino acid was preactivated by suspending 1 mmol of the first amino acid and 0.9 mmol HATU in 1 mL NMP and adding 2 mL of a 0.1 M solution of DIEA in NMP. After everything was dissolved, the mixture was allowed to stand for another 2 min before it was added to the resin. After shaking the suspension for 30 min, the resin was washed with DMF and Kaisertest was performed to confirm quantitative coupling. Double coupling was performed in the case that Kaisertest showed incomplete coupling. The synthesis cycle was repeated until the whole sequence was synthesized. The N-terminal Fmoc group was removed before cleaving the peptide from the resin using the methods described in Examples 1, 2, and 3. The crude compounds were analyzed by ESI-MS and HPLC.

Example 9

Synthesis and Characterization of Peptides Labeled with 6-ROX 50 mg of aHP-1 peptide on the resin were placed in a special fabricated glass column equipped with a glass frit, a stop-cocked outlet, and an argon inlet. The resin was washed with DMF and allowed to swell in DCM for 15 min, before the N-terminal Fmoc group was removed by adding 20% piperidine in DMF and shaking the suspension for 4 min. This procedure was repeated twice. The resin was washed with DMF. 0.1 mmol of the O-spacer (34.8 mg) together with 0.09 mmol HATU (34 mg) were suspended of the first amino acid and 0.9 mmol in 0.3 mL NMP and 0.2 mL of a 1 M solution of DIEA in NMP were added. After everything was dissolved, the mixture was allowed to stand for another 2 min before it was added to the resin. After shaking the suspension for 30 min, the resin was washed with DMF and Kaisertest was performed to confirm quantitative coupling. Double coupling was performed in the case Kaisertest showed incomplete coupling. 10 mg (19 $\mu$mol) 6-ROX and 6.5 mg (17 $\mu$mol) HATU were suspended in 0.5 mL NMP and 40 $\mu$L of a 1 M solution of DIEA in NMP were added. After shaking the mixture for 3 min it was added to the resin and the suspension was shaken overnight. The resin was washed with DMF and DCM and the labeled peptide was cleaved as desribed in Examples 1, 2, and 3. The crude compounds were purified by HPLC as described in Examples 4 and 5 and analyzed by ESI-MS and HPLC.

Example 10

Synthesis and Characterization of Peptides Labeled with OrG 488

50 mg of aHP-1 peptide on the resin were placed in a special fabricated glass column equipped with a glass fritt, a stop-cocked outlet and an argon inlet. The resin was washed with DMF and allowed to swell in DCM for 15 min, before the N-terminal Fmoc group was removed by adding 20% piperidine in DMF and shaking the suspension for 4 min. This procedure was repeated twice. The resin was washed with DMF. 0.1 mmol of the O-spacer (34.8 mg) together with 0.09 mmol HATU (34 mg) were suspended of the first amino acid and 0.9 mmol in 0.3 mL NMP and 0.2 mL of a 1 M solution of DIEA in NMP were added. After everything was dissolved, the mixture was allowed to stand for another 2 min before it was added to the resin. After shaking the suspension for 30 min, the resin was washed with DMF and Kaisertest was performed to confirm quantitative coupling. Double coupling was performed in the case Kaisertest showed incomplete coupling. 10 mg (24 µmol) OrG 488 and 8.3 mg (22 µmol) HATU were suspended in 0.5 mL NMP and 50 µL of a 1 M solution of DIEA in NMP were added. After shaking the mixture for 3 min it was added to the resin and the suspension was shaken overnight. The resin was washed with DMF and DCM and the labeled peptide was cleaved as described in Examples 1, 2, and 3. The crude compounds were purified by HPLC as described in Examples 4 and 5 and analyzed by ESI-MS and HPLC.

Example 11

Synthesis of PNA-peptide Conjugates

PNA-peptide conjugates were synthesized in a 5 µmole scale by using the corresponding peptide on the resin. Therefore the resin (ca. 50–60 mg) was placed special fabricated glass column equipped with a glass fritt, a stop-cocked outlet and an argon inlet. The resin was washed with DMF and allowed to swell in DCM for 15 min, before the N-terminal Fmoc group was removed by adding 20% piperidine in DMF and shaking the suspension for 4 min. This procedure was repeated twice. Then, the O-spacer was introduced by using the protocol described for coupling of the PNA monomers below. The PNA part of the conjugate was assembled by Fmoc chemistry, using commercially available Fmoc PNA monomers. One synthesis cycle involved the following steps: (i) Fmoc cleavage with 20% piperidine in DMF (2×1.5 min), (ii) DMF wash (5×), (iii) preactivation of the PNA monomer using HAT (0.9 equiv.) and DIEA (2.0 equiv) for 1–2 min, (iv) coupling for 40 min, (v) DMF wash (5×). Qualitative Kaisertest was performed to determine the coupling efficiency and double coupling was performed if Kaisertest indicated incomplete coupling. The N-terminal Fmoc group was removed by piperidine treatment described above and the resin was washed with DMF and DCM. The PNA-peptide conjugate was cleaved, deprotected and purified by HPLC as described in Examples 4 and 5. The following table shows the PNAs conjugated to amphipathic peptides, which have been synthesized and characterized.

TABLE 1

PNA-peptide conjugates.

| Isis # | Peptide | Sequence (N→C) | MW$_{calc}$ | MW$_{found}$ |
|---|---|---|---|---|
| 287069 | aHP-16 | CTCAGCACATCTACA-X-GKKALKLAAKLLKK-NH$_2$ (SEQ ID NO:24) | 5628.0 | 5532 |
| 287071 | aHP-24 | CTCAGCACATCTACA-X-GRRAFRRARRRFRR-NH$_2$ (SEQ ID NO:25 | 6035.3 | 6035 |
| 287075 | aHP-8 | CTCAGCACATCTACA-X-GKXKKKGAGKGFFA-NH$_2$ (SEQ ID NO:26 | 5569.8 | NA |
| 287073 | aHP-12 | CTCAGCACATCTACA-X-GKKLWKLWLKLWKK-NH$_2$ (SEQ ID NO:27 | 5973.5 | NA |
| 287074 | aHP-14 | CTCAGCACATCTACA-X-GKKWFKWFWKFFKK-NH$_2$ (SEQ ID NO:28 | 6109.5 | NA |
| 287070 | aHP-21 | CTCAGCACATCTACA-X-GKKAFKERAEKGFKK-NH$_2$ (SEQ ID NO:29 | 5713.9 | 5714 |
| 287072 | aHP-29 | CTCAGCACATCTACA-X-GKKPFKPPPKPFKK-NH$_2$ (SEQ ID NO:30 | 5742.1 | 5742 |

X = O-spacer

Example 12

Synthesis of PNA-peptide Conjugates Labeled with OrG 488

PNA-peptide conjugates were synthesized by using the corresponding peptide on the resin in a 2–3 µmole scale. Therefore the resin (ca. 20 mg) was placed in a small synthesis column for the 394 DNA/RNA Synthesizer and the O-spacer was introduced after cleavage of the N-terminal Fmoc group. After automated synthesis of the PNA part of the conjugate by Fmoc chemistry, another O-spacer was introduced and the resin was placed into a special fabricated glass column equipped with a glass fritt, a stop-cocked outlet and an argon inlet. The resin was washed with DMF and allowed to swell in DCM for 15 min, before the N-terminal Fmoc group was removed by adding 20% piperidine in DMF and shaking the suspension for 4 min. This procedure was repeated twice. 10 mg (24 µmol) OrG 488 and 8.3 mg (22 µmol) HATU were suspended in 0.5 mL NMP and 50 µL of a 1 M solution of DIEA in NMP were added. After shaking the mixture for 3 min it was added to the resin and the suspension was shaken overnight. The resin was washed with DMF and DCM, the labeled peptide was cleaved as described in Examples 1, 2, and 3. The crude compounds were purified by HPLC as described in Examples 4 and 5 and analyzed by ESI-MS and HPLC. The following table shows the PNA conjugates with the amphipathic peptides.

synthesis is carried out using an Applied Biosystems 433 A Peptide Synthesizer according to previously published procedures for PNA synthesis (Boc chemistry), such as those described in L. Christensen, et al. (1995), *J. Pept. Sci.* 1, 175–183; T. Koch, et al. (1997), *J. Pept. Res.* 49, 80–88. The synthesis of the peptide part of the conjugate is carried out

TABLE 2

PNA-peptide conjugates labeled with OrG 488 (known cellular permeation peptides).

| Isis # | Peptide | Sequence (N→C) | $MW_{calc}$ | $MW_{found}$ |
|---|---|---|---|---|
| 228018 | aHP-1 | OrG-X-CTCAGCACATCTACA-X-GKKAFKGAGKGFKK-NH$_2$ (SEQ ID NO:31) | 6107.9 | 6108.3 |
| 228019 | aHP-2 | OrG-X-CTCAGCACATCTACA-X-GRRAFRGAGRGFRR-NH$_2$ (SEQ ID NO:32) | 6276.0 | 6276.4 |
| 228027 | aHP-24 | OrG-X-CTCAGCACATCTACA-X-GRRAFRRARRRFRR-NH$_2$ (SEQ ID NO:25) | 6573.4 | 6574.0 |
| 228020 | aHP-8 | OrG-X-CTCAGCACATCTACA-X-GKKKKKGAGKGFFA-NH$_2$ (SEQ ID NO:26) | 6107.9 | 6108.6 |
| 228021 | aHP-11 | OrG-X-CTCAGCACATCTACA-X-GKKLFKLFLKLFKK-NH$_2$ (SEQ ID NO:33) | 6394.4 | 6394.7 |
| 228022 | aHP-12 | OrG-X-CTCAGCACATCTACA-X-GKKLWKLWLKLWKK-NH$_2$ (SEQ ID NO:27) | 6511.5 | 6511.4 |
| 228023 | aHP-14 | OrG-X-CTCAGCACATCTACA-X-GKKWFKWFWKFFKK-NH$_2$ (SEQ ID NO:28) | 6647.6 | 6647.7 |
| 228024 | aHP-16 | OrG-X-CTCAGCACATCTACA-X-GKKALKLAAKLLKK-NH$_2$ (SEQ ID NO:24) | 6166.1 | 6166.4 |
| 228028 | aHP-25 | OrG-X-CTCAGCACATCTACA-X-GKKAWKAWAKAWKK-NH$_2$ (SEQ ID NO:34) | 6343.2 | 6343.5 |
| 228025 | aHP-17 | OrG-X-CTCAGCACATCTACA-X-GKKAFKQAQKQFKK-NH$_2$ (SEQ ID NO:35) | 6321.1 | 6321.7 |
| 228026 | aHP-21 | OrG-X-CTCAGCACATCTACA-X-GKKAFKERAEKGFKK-NH$_2$ (SEQ ID NO:29) | 6252.0 | 6252.9 |
| 228029 | aHP-27 | OrG-X-CTCAGCACATCTACA-X-GKKAFKPAPKGFKK-NH$_2$ (SEQ ID NO:36) | 6188.0 | 6188.4 |
| 228030 | aHP-29 | OrG-X-CTCAGCACATCTACA-X-GKKPFKPPPKPFKK-NH$_2$ (SEQ ID NO:30) | 6280.2 | 6281.0 |

Example 13

Synthesis of Peptide-PNA Conjugates

For the synthesis of peptide-PNA conjugates, the PNA part of the conjugates is assembled first on MBHA polystyrene resin, pre-loaded with N-α-Boc-Lys-N-ε-2-Cl-Z. The after introducing the O-spacer as a linker unit, according to the standard protocols for peptide synthesis by Boc-chemistry. Deprotection and cleavage of the conjugates from the resin is carried out as described in Examples 1, 2, and 3. The following table shows the peptide-PNA conjugates.

TABLE 3

Peptide-PNA conjugates.

| Peptide | Sequence (N→C) | $MW_{calc}$ |
|---|---|---|
| aHP-16 | GKKALKLAAKLLKK-X-CTCAGCACATCTACA-K-NH$_2$ (SEQ ID NO:35) | 5756.2 |
| aHP-24 | GRRAFRRARRRFRR-X-CTCAGCACATCTACA-K-NH$_2$ (SEQ ID NO:36) | 6163.5 |
| aHP-8 | GKKKKKGAGKGFFA-X-CTCAGCACATCTACA-K-NH$_2$ (SEQ ID NO:37) | 5698 |
| aHP-12 | GKKLWKLWLKLWKK-X-CTCAGCACATCTACA-K-NH$_2$ (SEQ ID NO:38) | 6101.7 |
| aHP-14 | GKKWFKWFWKFFKK-X-CTCAGCACATCTACA-K-NH$_2$ (SEQ ID NO:39) | 6237.7 |
| aHP-21 | GKKAFKERAEKGFKK-X-CTCAGCACATCTACA-K-NH2 (SEQ ID NO:40) | 5842.0 |
| aHP-29 | GKKPFKPPPKPFKK-X-CTCAGCACATCTACA-K-NH$_2$ (SEQ ID NO:41) | 5870.3 |

X = O-spacer

Example 14

Synthesis of Oligonucleotide-peptide Conjugates

Oligonucleotide-peptide conjugates are prepared by first synthesizing the corresponding peptide. Therefore, the C-terminal amino acid of the sequence is loaded on HMBA PS resin (s. Examples 6 and 7). The resin (0.1 mmol $NH_2$) is placed into a special fabricated glass column equipped with a glass fritt, a stop-cocked outlet and an argon inlet. The resin is washed with DMF and DCM, before the N-terminal Boc group is removed by adding TFA/m-cresol (95:5) and shaking the suspension for 4 min. This procedure is repeated once. The resin is washed with DCM and DMF and the next amino acid is preactivated by suspending 1 mmol of the first amino acid and 0.9 mmol HATU in 1 mL NMP and adding 2 mL of a 0.1 M solution of DIEA in NMP. After everything is dissolved, the mixture is allowed to stand for another 2 min before it is added to the resin. After shaking the suspension for 30 min, the resin is washed with DMF and Kaisertest is performed to confirm quantitative coupling. Double coupling is performed in the case that Kaisertest shows incomplete coupling. The synthesis cycle is repeated until the whole sequence is synthesized. A portion of the resin is removed and treated with TFA/m-cresol (95:5) for a prolonged time to remove the N-terminal Boc-protection and any other acid-labile side chain protecting groups still present. After washing the resin with DCM and acetonitrile peptide is cleaved with aqueous $NH_3$ and analyzed by HPLC and ESI-MS after evaporation of the ammonia solution. Before oligonucleotide synthesis, the resin is treated with TFA/m-cresol (95:5) for a prolonged time as mentioned above and washed with DCM and DMF. DMT-protected γ-hydroxybutyric acid is coupled onto the N-terminal amino group using the amino acid coupling conditions described above. Unprotected side chain functionalities are acetylated using an extended capping step with acetic anhydride/pyridine/NMP (1:2:2). The oligonucleotide part of the conjugate is synthesized by standard phosphoramidite chemistry. Deprotection, purification and analysis of the oligonucleotides is performed as described in Examples 2, 3, and 5.

Table 4 shows the oligonucleotide conjugates with the amphipathic peptides.

TABLE 4

Oligonucleotide-peptide conjugates.

| Name | Sequence 5'→3' (N→C) | Modification | $MW_{calc}$ |
|---|---|---|---|
| 116847-aHP-1 | <u>CTG CTA</u> GCC TCT GGA <u>TTT GA</u>-X-GKKAFKGAGKGFKK (SEQ ID NO:42) | _ = 2'-MOE; X = γ-hydroxybutyryl | |
| 116847 aHP-2 | <u>CTG CTA</u> GCC TCT GGA <u>TTT GA</u>-X-GRRAFRGAGRGFRR (SEQ ID NO:43) | _ = 2'-MOE; X = γ-hydroxybutyryl | |

Example 15

Synthesis of Oligonucleotide-2'- or 3'-Peptide Conjugates

Oligonucleotide-2'- or 3'-peptide conjugates are prepared by synthesizing the oligonucleotide onto the N-terminus of the corresponding peptide on the resin. First, the C-terminal amino acid of the sequence is loaded on HMBA PS resin (s. Examples 6 and 7) and the peptide is assembled on the resin (initial loading of about 0.1–0.2 mmol $NH_2$/g) as described in Example 2. Prior to oligonucleotide synthesis, the resin is treated with TFA/m-cresol (95:5) for a prolonged time to remove any residual side chain protecting groups from the peptide, washed with DCM and DMF. DMT-protected γ-hydroxybutyric acid is coupled onto the N-terminal amino group using the amino acid coupling conditions described above. Unprotected side chain functionalities are acetylated using an extended capping step with acetic anhydride/pyridine/NMP (1:2:2). Then, the oligonucleotide part of the conjugate is synthesized by phosphoramidite chemistry using suitably protected phosphoramidite building blocks. Deprotection, purification and analysis of the conjugates is performed as outlined in Examples 2 and 5. The following table shows an oligonucleotide conjugated to different amphipathic peptides.

TABLE 5

Oligonucleotide-peptide conjugates.

| Name | Sequence 5'→3' (N→C) | Modification | $MW_{calc}$ |
|---|---|---|---|
| 116847-aHP-1 | <u>CTG CTA</u> GCC TCT GGA <u>TTT GA</u>-X-GKKAFKGAGKGFKK (SEQ ID NO:42) | backbone: all PS; _ = 2'-MOE; X = γ-hydroxybutyryl | 8829.9 |
| 116847-aHP-2 | <u>CTG CTA</u> GCC TCT GGA <u>TTT GA</u>-X-GRRAFRGAGRGFRR (SEQ ID NO:43) | backbone: all PS; _ = 2'-MOE; X = γ-hydroxybutyryl | 8998.0 |

Example 16

Solution Phase Synthesis of Oligonucleotide-5'-peptide Conjugates

For synthesis of oligonucleotide-5'-peptide conjugates, the oligonucleotide and the peptide oligomers are synthesized and purified separately following standard synthesis procedures of phosphoramidite and Fmoc-or Boc-chemistry, respectively. The peptide carries a C-terminal Cys, which provides a thiol group for conjugation. The oligonucleotide is modified with a linker carrying a primary amino function, which is introduced during solid phase synthesis using a commercially available building block (e.g. MMT amino-link phosphoramidite, Applied Biosystems) according to the manufacturer's protocol. After cleavage, deprotection and purification of the oligonucleotide, the primary amino function is further modified using a commercially available heterobifunctional cross-linking reagent (Sulfo-SMCC, Pierce) according to the manufacturer's protocol using 20 mM sodium phosphate, 0.15 M NaCl buffer, pH 7 for the coupling reaction and a 10-fold molar excess of the NHS-ester. After purification of the oligonucleotide carrying the terminal maleimide functionality by size exclusion chromatography (Sephadex G25), the conjugation is carried out according to the manufacturer's protocols with the maleimide-functionalized oligonucleotide and the thiol-containing peptide using a 1:1 molar ratio and the conjugation buffer described above (s. Scheme 1, c). The following table shows the peptide-oligonucleotide conjugates.

TABLE 6

Peptide-oligonucleotide conjugates.

| Name | Sequence N→C (5'→3') | Modification | MW$_{calc}$. |
|---|---|---|---|
| aHP1-116847 | GKKAFKGAGKGFKKC-X-<u>CTG CTA</u> GCC TCT GGA <u>TTT GA</u> (SEQ ID NO:44) | backbone: all PS; _ = 2'-MOE; | 9742 |
| aHP2-116847 | GRRAFRGAGRGFRRC-X-<u>CTG CTA</u> GCC TCT GGA <u>TTT GA</u> (SEQ ID NO:45) | backbone: all PS; _ = 2'-MOE; | 9910 |

Example 17

Fluorescence Microscopy to Evaluate Cellular Uptake of the Peptides

T24 cells were incubated with peptide conjugates, which were fluorescently labeled with 6-ROX for 30 min at 37° C. in PBS buffer. Then, the cells were washed, fixed with 4% PFA, and stained with DAPI. The slides were sealed and analyzed by fluorescence microscopy. Images were taken with constant exposure time and the uptake of the conjugates was evaluated by the intensity and distribution of the staining. Tables 7 and 8 show the summarized results from this study.

TABLE 7

Fluorescence microscopy with known peptides.

| Isis# | Name | Stain | Comment |
|---|---|---|---|
| 195726 | Transportan | Intense | Intense perinuclear staining |
| 195729 | pAntp | Low | Diffuse throughout (extracelluar?) |
| 195725 | HIV tat | Low | Perinuclear granular with nuclear bodies |
| 195728 | Arg Rich | Intense | Intense Perinuclear Staining |
| 195724 | PTD5 | Intense | Diffuse nuclear staining with nuclear bodies |
| 195727 | KFF | Intense | Diffuse nuclear staining |

TABLE 8

Fluorescence microscopy with novel amphipathic peptides.

| Isis # | Name | Stain | Comments |
|---|---|---|---|
| 195703 | aHP-1 | Low | |
| 195704 | aHP-2 | Moderate | Diffuse throughout cell with some nuclear bodies |
| 195705 | aHP-3 | Low | |
| 195706 | aHP-4 | Low | |
| 202439 | aHP-23 | Low | |
| 195707 | aHP-5 | Low | |
| 195708 | aHP-6 | Low | |
| 202440 | aHP-24 | Moderate | Trend towards extranuclear |
| 197428 | aHP-7 | Low | |
| 197429 | aHP-8 | Low | |
| 195709 | aHP-9 | Low | |
| 202441 | aHP-25 | Low | |
| 195710 | aHP-10 | Low | |
| 195711 | aHP-11 | Moderate | Perinuclear |
| 202442 | aHP-26 | Low | |

TABLE 8-continued

Fluorescence microscopy with novel amphipathic peptides.

| Isis # | Name | Stain | Comments |
|---|---|---|---|
| 195712 | aHP-12 | Moderate | Intense cytoplasmic with some nuclear bodies |
| 197432 | aHP-13 | Low | |
| 197433 | aHP-14 | Intense | Perinuclear and cytoplasmic with nuclear bodies |
| 197434 | aHP-15 | Low | |
| 197435 | aHP-16 | Low | |
| 195713 | aHP-17 | Low | |
| 195714 | aHP-18 | Low | |
| 195715 | aHP-19 | Low | |
| 195716 | aHP-20 | Low | |
| 197430 | aHP-21 | Low | |
| 197431 | aHP-22 | Low | |
| 202443 | aHP-27 | Low | |
| 202444 | aHP-28 | Low | |
| 202445 | aHP-29 | Low | |

Example 18

Figure 2:
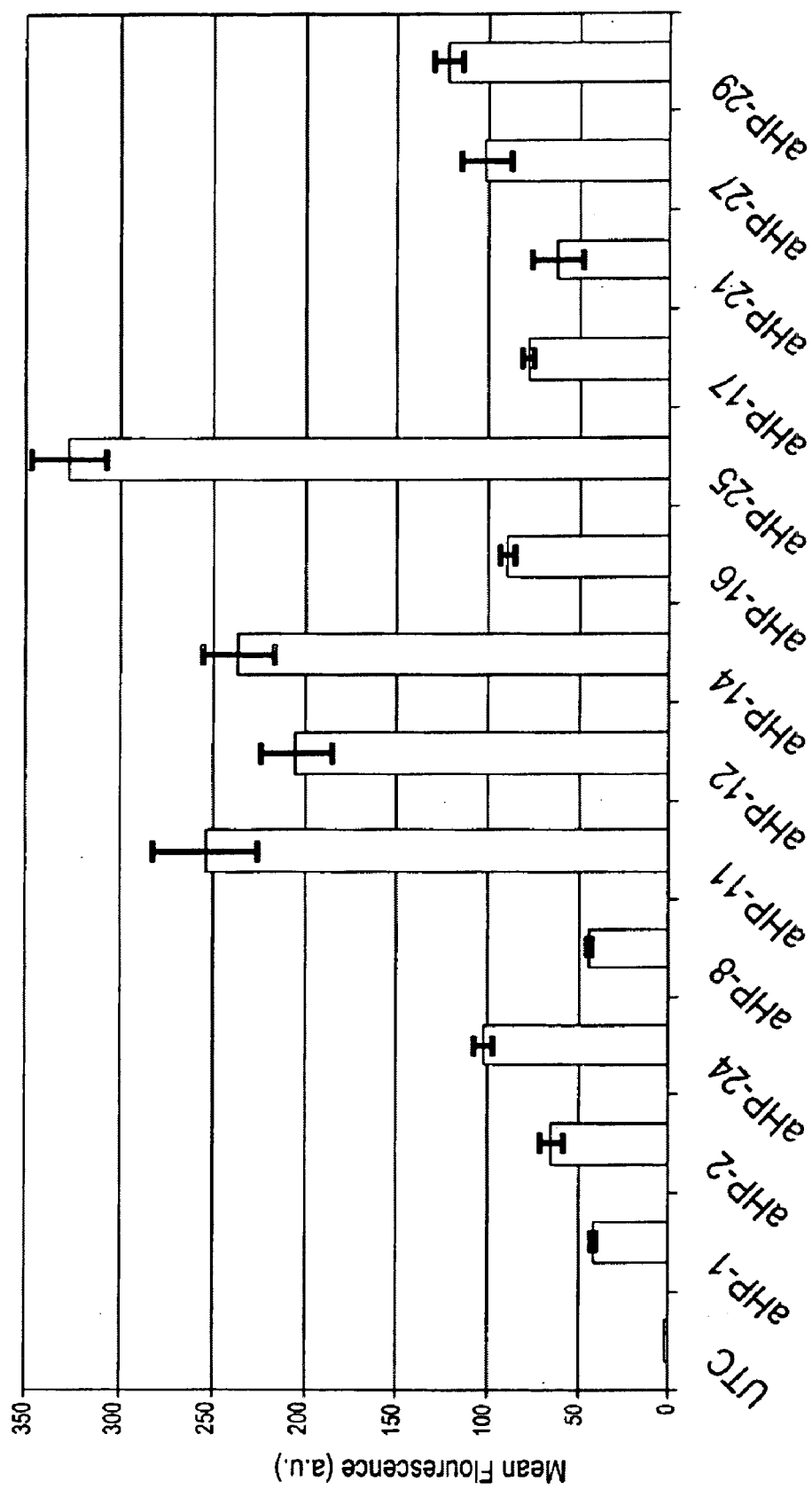
FIG. 2 shows the mean fluorescence of cells incubated with novel amphipathic peptides.

Flow Cytometry to Evaluate Cellular Uptake of the Peptides $10^5$ Jurkat cells per sample were incubated with OrG 488-labeled peptides at 37° C. in serum-containing RMPI for 3 h. Flow cytometry was performed with live cells after washing the cells and histograms were recorded. FIGS. 1 and 2 show the mean fluorescence as a measure of cellular uptake for the series of known and novel amphipathic peptides, respectively. The results underline the positive effect of Arg and hydrophobic amino acid residues (Trp, Phe, Ala, Leu) on the cellular uptake and confirm the results of Example 17.

Example 19

Effect of PNA-peptide Conjugates on PTEN Expression

Figure 3:
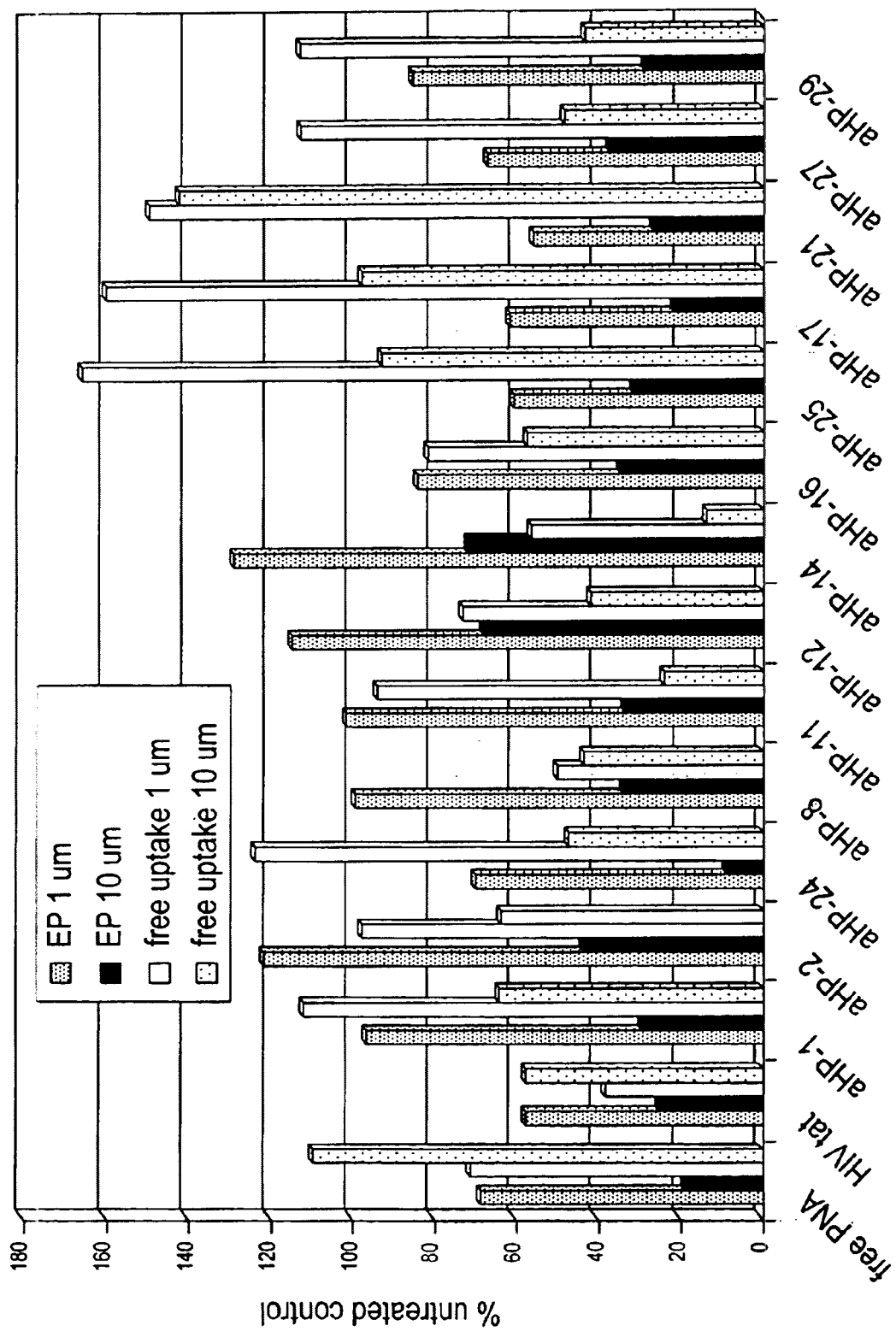
FIG. 3 shows the effect of PNA-peptide conjugates on PTEN protein expression and shows a comparison of electroporation (EP) and free uptake at 1 and 10 μM concentration.

BCL1 (3×10⁶) cells were plated into 60 mm dishes containing the noted concentrations of OrG 488-labeled PNA-peptide conjugates in 2.0 ml complete media (containing 10% serum) for 3 hours at 37° C./5% $CO_2$. Following the three hour initial incubation, 3.0 ml of complete media was added (5.0 ml final volume) and incubation was continued for 45 hours. Cells were harvested in 0.5 ml lysis buffer, spun (10 k rpm, 15', 4° C.) and the supernatant was quantitated for protein concentration. SDS-PAGE was performed on 50 ug samples and Western blots prepared (1° Ab-rabbit anti-human PTEN, 1:1000, Cell Signaling Technology #9552; 2° Ab Goat anti Rabbit-HRPO 1:10 k, BD Biosciences #RR14745) and developed by ECL Plus (Amersham). Imaging and quantitation was completed by Molecular Devices Typhoon Scanner and ImageQuant software. FIG. 3 compares the effect of PNA-peptide conjugates introduced into cells by electroporation or by free uptake on PTEN expression.

We claim:

1. An oligomeric compound having formula I:

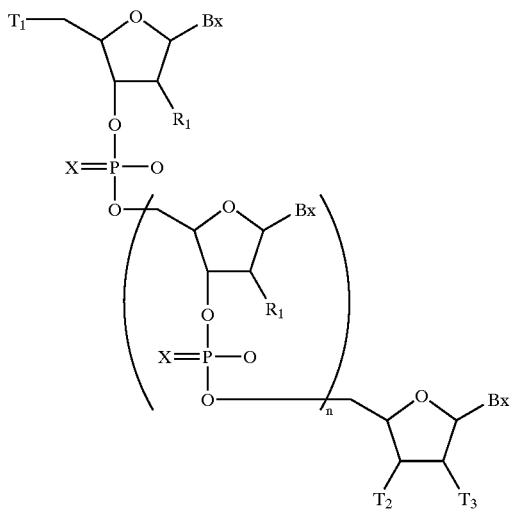

wherein:
one of $T_1$, $T_2$, and $T_3$ is L—$R_2$;
another of $T_1$, $T_2$, and $T_3$ is hydrogen, hydroxyl or a protected hydroxyl;
the remaining of $T_1$, $T_2$, and $T_3$ is hydrogen, L—$R_2$ or an optionally protected sugar substituent group;
each L is a linking moiety;
each $R_2$ is, independently, an amphipathic peptide having formula II:

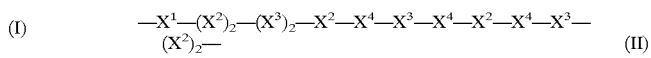

wherein
each $X^1$ is glycine;
each $X^2$ is, independently, lysine, arginine, ornithine or homoarginine;
each $X^3$ is, independently, alanine, valine, leucine, isoleucine, phenylalanine, tyrosine, tryptophan, cysteine, or methionine; and
each $X^4$ is, independently, lysine, arginine, ornithine, homoarginine, alanine, valine, leucine, isoleucine, phenylalanine, tyrosine, tryptophan, cysteine, methionine, glycine, serine, threonine, aspartate, glutamate, asparagine, or glutamine;
each Bx is an optionally protected heterocyclic base moiety;
each $R_1$ is, independently, hydrogen or an optionally protected sugar substituent group;
each X is, independently, S or O; and
n is from 2 to about 50.

2. The oligomeric compound of claim 1 wherein:
each $X^2$ is, independently, lysine or arginine;
each $X^3$ is, independently, alanine, leucine, phenylalanine or tryptophan; and
each $X^4$ is, independently, lysine, arginine, ornithine, homoarginine, alanine, valine, leucine, isoleucine, phenylalanine, tyrosine, tryptophan, cysteine, methionine or glycine.

3. The oligomeric compound of claim 2 wherein each $R_2$ is, independently:

-GRRAFRGAGRGFRR; or      (SEQ ID NO:2)

-GKKALKLAAKLLKK.         (SEQ ID NO:18)

4. The oligomeric compound of claim 3 wherein each $R_2$ is, independently:

-RRAFRGAGRGFRR.          (SEQ ID NO:2)

5. The oligomeric compound of claim 1 wherein each linking moiety is, independently, succinyl, substituted or unsubstituted $C_1$–$C_{10}$ alkyl, substituted or unsubstituted $C_2$–$C_{10}$ alkenyl or substituted or unsubstituted $C_2$–$C_{10}$ alkynyl, wherein the substituent groups are one or more groups selected from hydroxyl, amino, alkoxy, carboxy, benzyl, phenyl, nitro, thiol, thioalkoxy, halogen, alkyl, aryl, alkenyl and alkynyl.

6. The oligomeric compound of claim 1 wherein at least one of said linking moieties has formula III:

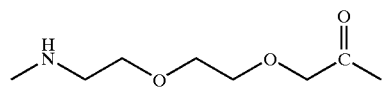

(III)

7. The oligomeric compound of claim 1 wherein $T_1$ is —L—$R_2$.

8. The oligomeric compound of claim 1 wherein $T_2$ is —L—$R_2$.

9. The oligomeric compound of claim 1 wherein $T_3$ is —L—$R_2$.

10. The oligomeric compound of claim 1 comprising two —L—$R_2$ groups.

11. The oligomeric compound of claim 10 wherein $T_1$ and one of $T_2$ and $T_3$ are each independently, —L—$R_2$.

12. The oligomeric compound of claim 1 further comprising a targeting moiety.

13. The oligomeric compound of claim 12 wherein said targeting moiety is covalently attached to said oligomeric compound at one of $T_1$, $T_2$ or $T_3$.

14. The oligomeric compound of claim 12 wherein said targeting moiety is covalently attached to $R_2$.

15. The oligomeric compound of claim 1 wherein said sugar substituent group is $C_1$–$C_{20}$ alkyl, $C_2$–$C_{20}$ alkenyl, $C_2$–$C_{20}$ alkynyl, $C_5$–$C_{20}$ aryl, —O-alkyl, —O-alkenyl, —O-alkynyl, —O-alkylamino, —O-alkylalkoxy, —O-alkylaminoalkyl, —O-alkyl imidazole, —OH, —SH, —S-alkyl, —S-alkenyl, —S-alkynyl, —N(H)-alkyl, —N(H)-alkenyl, —N(H)-alkynyl, —N(alkyl)$_2$, —O-aryl, —S-aryl, —NH-aryl, —O-aralkyl, —S-aralkyl, —N(H)-aralkyl, phthalimido (attached at N), halogen, amino, keto (—C(=O)—$R_a$), carboxyl (—C(=O)OH), nitro (—NO$_2$), nitroso (—N=O), cyano (—CN), trifluoromethyl (—CF$_3$), trifluoromethoxy (—O—CF$_3$), imidazole, azido (—N$_3$), hydrazino (—N(H)—NH$_2$), aminooxy (—O—NH$_2$), isocyanato (—N=C=O), sulfoxide (—S(=O)—$R_a$), sulfone (—S(=O)$_2$—$R_a$), disulfide (—S—S—$R_a$), silyl, heterocyclyl, carbocyclyl, an intercalator, a reporter group, a conjugate group, polyamine, polyamide, polyalkylene glycol or a polyether wherein each $R_a$ is, independently, hydrogen, a protecting group or substituted or unsubstituted alkyl, alkenyl, or alkynyl wherein the substituent groups are selected from haloalkyl, alkenyl, alkoxy, thioalkoxy, haloalkoxy, aryl, halogen, hydroxyl, amino, azido, carboxy, cyano, nitro, mercapto, a sulfide group, a sulfonyl group and a sulfoxide group;

or said sugar substituent group has one of formula $I_a$ or $II_a$:

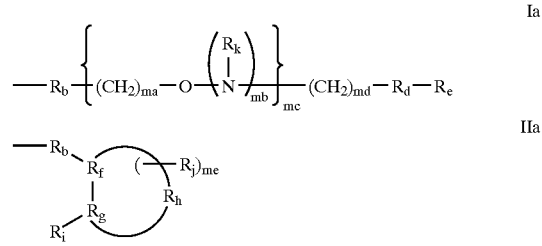

wherein:

$R_b$ is O, S or NH;

$R_d$ is a single bond, O, S or C(=O);

$R_e$ is $C_1$–$C_{10}$ alkyl, N($R_k$)($R_m$), N($R_k$)($R_n$), N=C($R_p$)($R_q$), N=C($R_p$)($R_r$) or has formula III$_a$;

$R_p$ and $R_q$ are each independently hydrogen or $C_1$–$C_{10}$ alkyl;

$R_f$ is —$R_x$—$R_y$;

each $R_s$, $R_t$, $R_u$ and $R_v$ is, independently, hydrogen, C(O)$R_w$, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group or a conjugate group, wherein the substituent groups are selected from hydroxyl, amino, alkynyl, carboxy, benzyl, phenyl, nitro, thiol, thioalkoxy, halogen, alkyl, aryl, alkenyl and alkynyl;

or optionally, $R_u$ and $R_v$, together form a phthalimido moiety with the nitrogen atom to which they are attached;

each $R_w$ is, independently, substituted or unsubstituted $C_1$–$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

$R_k$ is hydrogen, a nitrogen protecting group or —$R_x$—$R_y$;

$R_x$ is a bond or a linking moiety;

$R_y$ is a chemical functional group, a conjugate group or a solid support medium;

each $R_m$ and $R_n$ is, independently, H, a nitrogen protecting group, substituted or unsubstituted $C_1$–$C_{10}$ alkyl, substituted or unsubstituted $C_2$–$C_{10}$ alkenyl, or substituted or unsubstituted $C_2$–$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; NH$_3^+$, N($R_u$)($R_v$), guanidino and acyl where said acyl is an acid amide or an ester;

$R_i$ is OR$_z$, SR$_z$, or N(R$_z$)$_2$;

each $R_x$ is, independently, H, $C_1$–$C_8$ alkyl, $C_1$–$C_8$ haloalkyl, C(=NH)N(H)$R_u$, C(=O)N(H)$R_u$ or OC(=O)N(H)$R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, N($R_k$)($R_m$), O$R_k$, halo, S$R_k$ or CN;

ma is 1 to about 10;

each mb is, independently, 0 or 1;

mc is 0 or an integer from 1 to 10;

md is an integer from 1 to 10;

me is 0, 1 or 2; and provided that when mc is 0, md is greater than 1.

16. An oligomeric compound having formula IV:

(IV)

wherein:

each $T_4$ and $T_5$ is, independently, —L—$R_2$, hydrogen, an amino protecting group, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl, provided that at least one of $T_4$ and $T_5$ is —L—$R_2$;

each Bx is an optionally protected heterocyclic base moiety;

n is from 2 to about 50;

each L is a linking moiety; and each $R_2$ is, independently, an amphipathic peptide having formula II:

$$—X^1—(X^2)_2—(X^3)_2—X^2—X^4—X^3—X^4—X^2—X^4—X^3—(X^2)_2 \quad (II)$$

wherein $X^1$ is glycine;

each $X^2$ is, independently, arginine, ornithine or homoarginine;

each $X^3$ is, independently, alanine, valine, leucine, isoleucine, phenylalanine, tylosine, tryptophan, cysteine, or methionine; and each $X^4$ is, independently, lysine, arginine, ornithine, homoarginine, alanine, valine, leucine, isoleucine, phenylalanine, tyrosine, tryptophan, cysteine, methionine, glycine, serine, threonine, aspartate, glutamate, asparagine, or glutamine.

17. The oligomeric compound of claim 16 wherein:

each $X^2$ is, independently, lysine or arginine;

each $X^3$ is, independently, alanine, leucine, phenylalanine or tryptophan; and each $X^4$ is, independently, lysine, arginine, ornithine, homoarginine, alanine, valine, leucine, isoleucine, phenylalanine, tyrosine, tryptophan, cysteine, methionine or glycine.

18. The oligomeric compound of claim 17 wherein each $R_2$ is, independently:

| -GRRAFRGAGRGFRR; or | (SEQ ID NO:2) |
| -GKKALKLAAKLLKK. | (SEQ ID NO:18) |

19. The oligomeric compound of claim 18 wherein each $R_2$ is, independently:

| GRRAFRGAGRGFRR. | (SEQ ID NO:2) |

20. The oligomeric compound of claim 16 wherein each linking moiety is, independently, succinyl, substituted or unsubstituted $C_1$–$C_{10}$ alkyl, substituted or unsubstituted $C_2$–$C_{10}$ alkenyl or substituted or unsubstituted $C_2$–$C_{10}$ alkynyl, wherein the substituent groups are one or more groups selected from hydroxyl, amino, alkoxy, carboxy, benzyl, phenyl, nitro, thiol, thioalkoxy, halogen, alkyl, aryl, alkenyl and alkynyl.

21. The oligomeric compound of claim 16 wherein at least one of said linking moieities has formula III:

(III)

22. The oligomeric compound of claim 16 wherein $T_4$ is —L—$R_2$.

23. The oligomeric compound of claim 16 wherein $T_5$ is —L—$R_2$.

24. The oligomeric compound of claim 16 wherein $T_4$ and $T_5$ are each independently —L—$R_2$.

25. The oligomeric compound of claim 16 further comprising a targeting moiety.

26. The oligomeric compound of claim 25 wherein said targeting moiety is covalently attached to said oligomeric compound at one of $T_4$ or $T_5$.

27. The oligomeric compound of claim 25 wherein said targeting moiety is covalently attached to $R_2$.

28. An oligomeric compound having at least one peptide covalently bound thereto, wherein said peptide comprises from about 8 to about 20 amino acids and is capable of forming an α-helical structure having at least one hydrophobic face and at least one hydrophilic face; and said oligomeric compound further comprises at least one targeting moiety covalently attached thereto, wherein the oligomeric compound comprises at least one oligonucleotide, oligonucleoside, oligonucleotide analog, modified oligonucleotide, or oligonucleotide mimetic.

29. The oligomeric compound of claim 28 wherein the targeting moiety is covalently linked to the oligomeric compound.

30. The oligomeric compound of claim 28 wherein the targeting moiety is covalently linked to the peptide.

31. The oligomeric compound of claim 28 wherein the targeting moiety is a ligand that binds to a cell-surface protein.

32. The oligomeric compound of claim 28 wherein said targeting moiety is transferrin, folate, epidermal growth factor, nerve growth factor, insulin, alpha-fetoprotein, galactose, galactosamine, lactose, mannose, a polyclonal antibody, or a monoclonal antibody.

33. The oligomeric compound of claim 28 wherein the targeting moiety is Vitamin $B_{12}$, ibuprofen, cholesterol, or low-density lipoprotein.

34. The oligomeric compound of claim 28 wherein the targeting moiety is a peptide comprising an arginine-glycine-aspartic acid sequence.

35. The oligomeric compound of claim 28 wherein the oligomeric compound is an oligonucleotide, an oligonucleotide analog, a peptide nucleic acid, a morpholino nucleic acid, a cyclohexenyl nucleic acid, an anhydrohexitol nucleic acid, a locked nucleic acid, a bicyclic nucleic acid, a tricyclic nucleic acid, a phosphonomonoester nucleic acid or a cyclobutyl nucleic acid.

36. The oligomeric compound of claim 35 wherein the oligomeric compound is an oligonucleotide, an oligonucleotide analog, a peptide nucleic acid, a morpholino nucleic acid, a locked nucleic acid, or a bicyclic nucleic acid.

37. The oligomeric compound of claim 1 wherein each amphipathic peptide is capable of forming an α-helical structure.

38. The oligomeric compound of claim 16 wherein each amphipathic peptide is capable of forming an α-helical structure.

* * * * *

UNITED STATES PATENT AND TRADEMARK OFFICE
CERTIFICATE OF CORRECTION

| | |
|---|---|
| PATENT NO. | : 6,878,805 B2 |
| APPLICATION NO. | : 10/222595 |
| DATED | : April 12, 2005 |
| INVENTOR(S) | : Muthiah Manoharan et al. |

It is certified that error appears in the above-identified patent and that said Letters Patent is hereby corrected as shown below:

Column 80, line 33, please delete "$R_f$" and insert therefor -- $R_r$ --;

Column 81, line 1, please delete "$R_x$" and insert therefor -- $R_2$ --;

Column 81, line 65, please delete "leucme" and insert therefor -- lucine --;

Column 81, line 66, please delete "tylosine" and insert therefor -- tyrosine --.

Signed and Sealed this

Eleventh Day of July, 2006

JON W. DUDAS
*Director of the United States Patent and Trademark Office*

```
                        SEQUENCE LISTING

<160> NUMBER OF SEQ ID NOS: 45

<210> SEQ ID NO 1
<211> LENGTH: 14
<212> TYPE: PRT
<213> ORGANISM: Artificial Sequence
<220> FEATURE:
<223> OTHER INFORMATION: Synthetic construct

<400> SEQUENCE: 1

Gly Lys Lys Ala Phe Lys Gly Ala Gly Lys Gly Phe Lys Lys
 1               5                  10

<210> SEQ ID NO 2
<211> LENGTH: 14
<212> TYPE: PRT
<213> ORGANISM: Artificial Sequence
<220> FEATURE:
<223> OTHER INFORMATION: Synthetic construct

<400> SEQUENCE: 2

Gly Arg Arg Ala Phe Arg Gly Ala Gly Arg Gly Phe Arg Arg
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Synthetic construct

<400> SEQUENCE: 3

Gly Gly Lys Ala Phe Lys Gly Ala Gly Lys Gly Phe Lys Gly
 1               5                  10

<210> SEQ ID NO 4
<211> LENGTH: 14
<212> TYPE: PRT
<213> ORGANISM: Artificial Sequence
<220> FEATURE:
<223> OTHER INFORMATION: Synthetic construct

<400> SEQUENCE: 4

Gly Lys Lys Ala Phe Lys Gly Ala Gly Lys Gly Phe Lys Gly
 1               5                  10

<210> SEQ ID NO 5
<211> LENGTH: 14
```

```
<212> TYPE: PRT
<213> ORGANISM: Artificial Sequence
<220> FEATURE:
<223> OTHER INFORMATION: Synthetic construct

<400> SEQUENCE: 5

Gly Arg Arg Ala Phe Arg Gly Ala Gly Arg Gly Phe Arg Gly
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic construct

<400> SEQUENCE: 6

Gly Lys Lys Ala Phe Lys Gly Ala Gly Lys Lys Phe Lys Lys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic construct

<400> SEQUENCE: 7

Gly Lys Lys Ala Phe Lys Lys Ala Lys Lys Lys Phe Lys Lys
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic construct

<400> SEQUENCE: 8

Gly Arg Arg Ala Phe Arg Arg Ala Arg Arg Arg Phe Arg Arg
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic construct

<400> SEQUENCE: 9

Gly Lys Lys Ala Trp Lys Gly Ala Gly Lys Gly Trp Lys Lys
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic construct

<400> SEQUENCE: 10

Gly Lys Lys Ala Trp Lys Ala Trp Ala Lys Ala Trp Lys Lys
1               5                   10

<210> SEQ ID NO 11
<211> LENGTH: 14
<212> TYPE: PRT
```

```
<213> ORGANISM: Artificial Sequence
<220> FEATURE:
<223> OTHER INFORMATION: Synthetic construct

<400> SEQUENCE: 11

Gly Lys Lys Leu Phe Lys Gly Leu Gly Lys Gly Phe Lys Lys
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic construct

<400> SEQUENCE: 12

Gly Lys Lys Leu Phe Lys Leu Phe Leu Lys Leu Phe Lys Lys
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic construct

<400> SEQUENCE: 13

Gly Lys Lys Leu Trp Lys Gly Leu Gly Lys Gly Trp Lys Lys
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic construct

<400> SEQUENCE: 14

Gly Lys Lys Leu Trp Lys Leu Trp Leu Lys Leu Trp Lys Lys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic construct

<400> SEQUENCE: 15

Gly Lys Lys Trp Phe Lys Gly Trp Gly Lys Gly Phe Lys Lys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic construct

<400> SEQUENCE: 16

Gly Lys Lys Trp Phe Lys Trp Phe Trp Lys Phe Phe Lys Lys
1               5                   10

<210> SEQ ID NO 17
<211> LENGTH: 14
<212> TYPE: PRT
<213> ORGANISM: Artificial Sequence
```

```
<220> FEATURE:
<223> OTHER INFORMATION: Synthetic construct

<400> SEQUENCE: 17

Gly Lys Lys Ala Leu Lys Gly Ala Gly Lys Gly Leu Lys Lys
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic construct

<400> SEQUENCE: 18

Gly Lys Lys Ala Leu Lys Leu Ala Ala Lys Leu Leu Lys Lys
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Synthetic construct

<400> SEQUENCE: 19

Gly Lys Lys Ala Phe Lys Gln Ala Gln Lys Gln Phe Lys Lys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetic construct

<400> SEQUENCE: 20

Gly Lys Lys Ala Phe Lys Gly Ala Glu Lys Gly Phe Lys Lys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic construct

<400> SEQUENCE: 21

Gly Lys Lys Ala Phe Lys Glu Ala Gly Lys Gly Phe Lys Lys
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetic construct

<400> SEQUENCE: 22

Gly Lys Lys Ala Phe Lys Glu Ala Glu Lys Gly Phe Lys Lys
1               5                   10

<210> SEQ ID NO 23
<211> LENGTH: 15
<212> TYPE: PRT
<213> ORGANISM: Artificial Sequence
<220> FEATURE:
```

<223> OTHER INFORMATION: Synthetic construct

<400> SEQUENCE: 23

Gly Lys Lys Ala Phe Lys Glu Arg Ala Glu Lys Gly Phe Lys Lys
1               5                   10                  15

<210> SEQ ID NO 24
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      XGKKALKLAAKLAAKLLKK; X= O spacer

<400> SEQUENCE: 24
ctcagcacat ctaca                                              15

<210> SEQ ID NO 25
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      XGRRAFRRARRRFRR; X= O spacer

<400> SEQUENCE: 25
ctcagcacat ctaca                                              15

<210> SEQ ID NO 26
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      XGKKKKKGAGKGFFA; X= O-spacer

<400> SEQUENCE: 26
ctcagcacat ctaca                                              15

<210> SEQ ID NO 27
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      XGKKLWKLWLKLWKK; X= O-spacer

<400> SEQUENCE: 27
ctcagcacat ctaca                                              15

<210> SEQ ID NO 28
<211> LENGTH: 15
<212> TYPE: DNA

```
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      XGKKWFKWFWKFFKK; X= O-spacer

<400> SEQUENCE: 28
ctcagcacat ctaca                                                    15

<210> SEQ ID NO 29
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      XGKKAFKERAEKGFKK; X= O-spacer

<400> SEQUENCE: 29
ctcagcacat ctaca                                                    15

<210> SEQ ID NO 30
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      XGKKPFKPPPKPFKK; X= O-spacer

<400> SEQUENCE: 30
ctcagcacat ctaca                                                    15

<210> SEQ ID NO 31
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      XGKKAFKGAGKGFKK; X= O-spacer

<400> SEQUENCE: 31
ctcagcacat ctaca                                                    15

<210> SEQ ID NO 32
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      XGRRAFRGAGRGFRR; X= O-spacer

<400> SEQUENCE: 32
```

-continued ctcagcacat ctaca                                                    15

<210> SEQ ID NO 33
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      XGKKLFKLFLKLFKK; X= O-spacer

<400> SEQUENCE: 33
ctcagcacat ctaca                                                    15

<210> SEQ ID NO 34
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      XGKKAWKAWAKAWKK; X= O-spacer

<400> SEQUENCE: 34
ctcagcacat ctaca                                                    15

<210> SEQ ID NO 35
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      XGKKAFKQAQKQFKK; X= O-spacer

<400> SEQUENCE: 35
ctcagcacat ctaca                                                    15

<210> SEQ ID NO 36
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      XGKKAFKPAPKGFKK; X= O-spacer

<400> SEQUENCE: 36
ctcagcacat ctaca                                                    15

<210> SEQ ID NO 37
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature

```
<223> OTHER INFORMATION: Conjugated through a linking group to a
      peptide of sequence
      GKKALKLAAKLLKKX; X= O-spacer
<220> FEATURE:
<221> NAME/KEY: misc_feature
<223> OTHER INFORMATION: Conjugated through a linking group to a
      peptide of sequence
      GKKKKKGAGKGFFAX; X= O-spacer

<400> SEQUENCE: 37
ctcagcacat ctaca                                               15

<210> SEQ ID NO 38
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      GKKLWKLWLKLWKKX; X= O-spacer

<400> SEQUENCE: 38
ctcagcacat ctaca                                               15

<210> SEQ ID NO 39
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      GKKWFKWFWKFFKKX; X= O-spacer

<400> SEQUENCE: 39
ctcagcacat ctaca                                               15

<210> SEQ ID NO 40
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      GKKAFKERAEKGFKKX; X= O-spacer

<400> SEQUENCE: 40
ctcagcacat ctaca                                               15

<210> SEQ ID NO 41
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      GKKPFKPPPKPFKKX; X= O-spacer

<400> SEQUENCE: 41
```
ctcagcacat ctaca                                                15

<210> SEQ ID NO 42
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      XGKKAFKGAGKGFKK; X= y-hydroxybutyryl
<220> FEATURE:
<221> NAME/KEY: misc_feature
<222> LOCATION: (1)..(5)
<223> OTHER INFORMATION: 2'-MOE
<220> FEATURE:
<221> NAME/KEY: misc_feature
<222> LOCATION: (16)..(20)
<223> OTHER INFORMATION: 2'-MOE

<400> SEQUENCE: 42
ctgctagcct ctggatttga                                           20

<210> SEQ ID NO 43
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      XGRRAFRGAGRGFRR;X= y-hydroxybutyryl
<220> FEATURE:
<221> NAME/KEY: misc_feature
<222> LOCATION: (1)..(5)
<223> OTHER INFORMATION: 2'-MOE
<220> FEATURE:
<221> NAME/KEY: misc_feature
<222> LOCATION: (16)..(20)
<223> OTHER INFORMATION: 2'-MOE

<400> SEQUENCE: 43
ctgctagcct ctggatttga                                           20

<210> SEQ ID NO 44
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      GKKAFKGAGKGFKKCX; X= any amino acid
<220> FEATURE:
<221> NAME/KEY: misc_feature
<222> LOCATION: (1)..(5)
<223> OTHER INFORMATION: 2'-MOE
<220> FEATURE:
<221> NAME/KEY: misc_feature
<222> LOCATION: (1)..(20)
<223> OTHER INFORMATION: All PS Backbone
<220> FEATURE:
<221> NAME/KEY: misc_feature
<222> LOCATION: (16)..(20)
<223> OTHER INFORMATION: 2'-MOE

<400> SEQUENCE: 44

```
ctgctagcct ctggatttga                                          20

<210> SEQ ID NO 45
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Conjugated through a linking group to a
      peptide of sequence
      GRRAFRGAGRGFRRCX; X= any amino acid
<220> FEATURE:
<221> NAME/KEY: misc_feature
<222> LOCATION: (1)..(5)
<223> OTHER INFORMATION: '2-MOE
<220> FEATURE:
<221> NAME/KEY: misc_feature
<222> LOCATION: (1)..(20)
<223> OTHER INFORMATION: All PS backbone
<220> FEATURE:
<221> NAME/KEY: misc_feature
<222> LOCATION: (16)..(20)
<223> OTHER INFORMATION: '2-MOE

<400> SEQUENCE: 45
ctgctagcct ctggatttga                                          20
```